(12) United States Patent
Richard et al.

(10) Patent No.: US 7,827,038 B2
(45) Date of Patent: Nov. 2, 2010

(54) MASK FITTING SYSTEM AND METHOD

(75) Inventors: Ron Richard, Poway, CA (US); Sophear Su, Carramar (AU); Gary Christopher Robinson, North Ryde (AU); Philip Rodney Kwok, North Ryde (AU); John Michael Kelly, Drummoyne (AU); Andrew Martin Price, North Ryde (AU); Ivan John Vuletich, Epping (AU); Karthikeyan Selvarjan, North Ryde (AU)

(73) Assignee: ResMed Limited, Bella Vista, New South Wales (AU)

( * ) Notice: Subject to any disclaimer, the term of this patent is extended or adjusted under 35 U.S.C. 154(b) by 1086 days.

(21) Appl. No.: 10/556,461

(22) PCT Filed: Jun. 6, 2005

(86) PCT No.: PCT/AU2005/000810

§ 371 (c)(1),
(2), (4) Date: Nov. 10, 2005

(87) PCT Pub. No.: WO2005/118041

PCT Pub. Date: Dec. 15, 2005

(65) Prior Publication Data

US 2006/0235877 A1 Oct. 19, 2006

Related U.S. Application Data

(60) Provisional application No. 60/619,951, filed on Oct. 20, 2004, provisional application No. 60/576,621, filed on Jun. 4, 2004.

(51) Int. Cl.
*G06Q 10/00* (2006.01)
*G06Q 50/00* (2006.01)

(52) U.S. Cl. .......................................... 705/2

(58) Field of Classification Search ................ 705/2, 705/4, 153; 706/14; 707/104.1; 709/203; 382/154; 128/206.24; 248/279; 250/223; 351/206

See application file for complete search history.

(56) References Cited

U.S. PATENT DOCUMENTS 4,504,129 A * 3/1985 Van Iderstine .............. 351/206

(Continued)

FOREIGN PATENT DOCUMENTS

| DE | 101 38 416 | 2/2003 |
|----|------------|--------|
| EP | 1 116 492 | 7/2001 |
| FR | 2 824 739 | 11/2002 |
| WO | 00/059567 | 10/2000 |
| WO | 2004/037153 | 5/2004 |

OTHER PUBLICATIONS

U.S. Appl. No. 60/434,459, filed Dec. 18, 2002 as referenced in US PGPUB 2004/0133604 A1.*

(Continued)

*Primary Examiner*—Gerald J. O'Connor
*Assistant Examiner*—John A Pauls
(74) *Attorney, Agent, or Firm*—Nixon & Vanderhye P.C.

(57) ABSTRACT

A mask fitting system (1) for selecting a mask system for a patient includes at least one terminal (6) which receives data unique to a patient. The patient data can be scanned in using a scanner, such as a handheld or 3-D scanner, or the relevant dimensions of the patient can be simply input into the terminal. A database (2) is provided to store mask system data relating to a plurality of potential mask system solutions for the patient. A communication channel (4) is provided by which the data received by the terminal can be compared with mask system data stored in a mask system database, so as to generate a best-fit mask system result. The best-fit result may include one or more mask system recommendations for the patient.

61 Claims, 17 Drawing Sheets

U.S. PATENT DOCUMENTS

| | | | | | |
|---|---|---|---|---|---|
| 4,825,068 | A | * | 4/1989 | Suzuki et al. | 250/223 R |
| 5,284,313 | A | * | 2/1994 | Hallgren | 248/279.1 |
| 5,584,125 | A | | 12/1996 | Prete | |
| 5,771,310 | A | * | 6/1998 | Vannah | 382/154 |
| 6,017,315 | A | | 1/2000 | Starr et al. | |
| 6,397,847 | B1 | * | 6/2002 | Scarberry et al. | 128/206.24 |
| 6,546,356 | B1 | * | 4/2003 | Genest | 702/153 |
| 6,728,589 | B1 | | 4/2004 | Delache et al. | |
| 6,988,088 | B1 | * | 1/2006 | Miikkulainen et al. | 706/14 |
| 2002/0188664 | A1 | * | 12/2002 | Hultgren et al. | 709/203 |
| 2004/0133604 | A1 | * | 7/2004 | Lordo | 707/104.1 |

OTHER PUBLICATIONS http://www.cpap.com/cpap-mask-sizing.php, Mask Sizing Guide, 4 pages.

E2-DigiMask™ Nasal Version, "The effective Nasal CPAP Therapy Solution That Offers Many Key Benefits," (Aug. 2005), pp. 1-4.

Sensa Seal™, User Application Instructions, Reusable Silicone Rubber Seal Accessory Attachment for the Hans Rudolph 7500 & 7600 Series Oro-Nasal Masks (2004), 2 pgs.

Hans Rudolph 7600 Series Oro-Nasal (Full Face) CPAP/NPPV Mask, Instructions for Use and Recommendations for Cleaning, Disinfection, Sterilization & Maintenance (2005), 6 pgs.

International Search Report for PCT/AU2005/000810 dated Jul. 4, 2005.

Nasal Pillow FAQ from cpap-pro.net, Oct. 14, 2005, 4 pages.

Best Full Face Mask, groups.google.com/group/alt.support.sleep-disorder, Oct. 13, 2005, 10 pages.

Help with autopap/ultra mirage, groups.google.com/group/alt.support.sleep-disorder, Oct. 13, 2005, 13 pages.

Best Full Face Mask, groups.google.com/group/alt.support.sleep-disorder, Oct. 19, 2005, 10 pages.

European Search Report issued for European Patent Application No. 05747030.4-2320, dated Jul. 29, 2009.

Sullivan Nasal CPAP Products, "Mask Systems Handbook", Sep. 1993, pp. 1-12 (7 pages).

Respironics "Nasal Mask Fitting Kit Instruction Card" with Nasal Mask Sizing Gauge, circa May 25, 1994, 1 page.

Respironics Mask Fitting Box, 1994, 1 page.

Respironics Mask Fitting Box "Contour Mask Fitting Kit—Reorder #302190", 1994, 1 page.

ResMed Product Specification, Doc. No. R169-002, "Mask Fitting Template", 1995, 3 pages.

ResMed Brochure, "Clinical Equipment", 1997, 1 page.

ResMed Specification, Doc. No. 16954, "Disposable Mask Fitting Template" 1999, 3 pages.

ResMed Printed Material Specification, Doc. No. 16638, "Obsolete—Full Face Mask System—Fitting Template", 1999, 3 pages.

ResMed Printed Material Specification, Doc. No. 16956, "AWSL—Ultra Mirage Mask System—Fitting Template", 2001, 4 pages.

ResCare Blue Mask Fitting Template—Side 1, R169-002, 1 page.

ResCare Blue Mask Fitting Template—Side 2, R-169-002, 1 page.

Healthdyne Technologies, "The Softest, Silkiest CPAP Mask Available.", 2 pages.

ResCare Plastic Mask Fitting Template, 1 page.

ResCare Mask Fitting Template, 1 page.

Oct. 1997 Video of Mirage Mask System, 1 Compact Disc.

* cited by examiner

Fig. 4

Fig. 5

MASK FITTING SYSTEM AND METHOD

CROSS REFERENCE TO APPLICATION

This is a national phase application of PCT/AU2005/000810, filed Jun. 6, 2005, which application claims the benefit of U.S. Provisional Application Ser. No. 60/619,951, filed Oct. 20, 2004 and U.S. Provisional Application Ser. No. 60/576,621, filed Jun. 4, 2004, each incorporated herein by cross reference in its entirety.

BACKGROUND OF THE INVENTION

1. Field of the Invention

This application is directed to a mask fitting system. In particular, the invention relates to a system for selection of a mask for patients suffering from a sleeping disorder, such as obstructive sleep apnea.

2. Description of Related Art

There are several techniques which have been used in the past to fit mask systems to patients. In one example, a mask fitting template is used to obtain the necessary dimensions from the patient. Such mask fitting templates are available from ResMed Limited. In another example, a doctor or clinician will pick a mask system, such as ResMed's standard Ultra Mirage®, where a single mask system is believed to fit up to 80% of the population. Otherwise, the doctor or clinician selects a mask system for a patient simply by looking at the patient. Whichever technique or technique combination is used, selection of a mask system to obtain an optimal fit is limited by the knowledge of the clinician or doctor who is treating the patient.

With an ever increasing range of different masks available to fit a wide range of different people, it is increasingly difficult for clinicians or doctors to choose the most appropriate mask for the patient in the limited amount of time for fitting. The most appropriate fit, as used herein, may refer to the best human interface fit, maximum comfort, maximum seal and/or the best type of technology to suit a patient's circumstances, needs and preferences. Therefore, patients in some cases may not be fitted with a mask system that would best fit the patient, which may result in less effective treatment and/or less patient compliance.

Therefore, a need has arisen to develop a system to allow for convenient and automated selection of a patient's mask system.

BRIEF SUMMARY OF THE INVENTION

One aspect of the invention aims to ameliorate one or more of the above noted problems.

Another aspect of the invention is to match the patient with the most appropriate mask system, thereby improving the effectiveness of treatment and overall patient compliance.

Another aspect of the invention is directed to a mask fitting system for a patient, including at least one terminal to receive patient data unique to the patient, a mask system database to store mask system data relating to a plurality of mask systems and a communication channel by which patient data received in the terminal can be compared with mask system data stored in the mask system database so as to best match the patient with at least one preferred mask system selected from the plurality of mask systems in the mask system database.

Another aspect of the invention is directed to a terminal which is configured to receive patient data, communicate at least a portion of the patient data to a mask system database and display a best-fit mask result in accordance with a comparison of the patient data and mask system data of the mask system database.

Still another aspect of the invention is directed to a mask system database which is configured to store mask system data for a plurality of mask systems, receive from a terminal patient data, and generate a best-fit mask system result based on a comparison of the patient data and the mask system data Although the mask fitting system is described in relation to mask systems for patients who suffer from obstructive sleep apnea, the mask fitting system is not limited to such applications and may be provided to select patient interfaces and/or their accessories, such as headgear, for patients who suffer from other disorders. The mask fitting system may also be used as simply a method to record clinical details. Moreover, the mask fitting system can be used to select a mask/components for users who do not suffer from disorders, e.g., occupational health and safety masks.

These and other aspects of the invention will be described in or apparent from the following detailed description of preferred embodiments.

BRIEF DESCRIPTION OF THE DRAWINGS

Preferred embodiments of the invention will be described in relation to the following drawings in which:

FIGS. 4, 5, 6, 7A, 7B and 8 illustrate sequential exemplary screen shots of a mask fitting program in use, according to an embodiment of the present invention;

FIGS. 7B-1 TO 7B-3 illustrate exemplary methods for obtaining mask fit dimensions according to embodiments of the present invention;

DETAILED DESCRIPTION OF PREFERRED EMBODIMENTS

Figure 1:
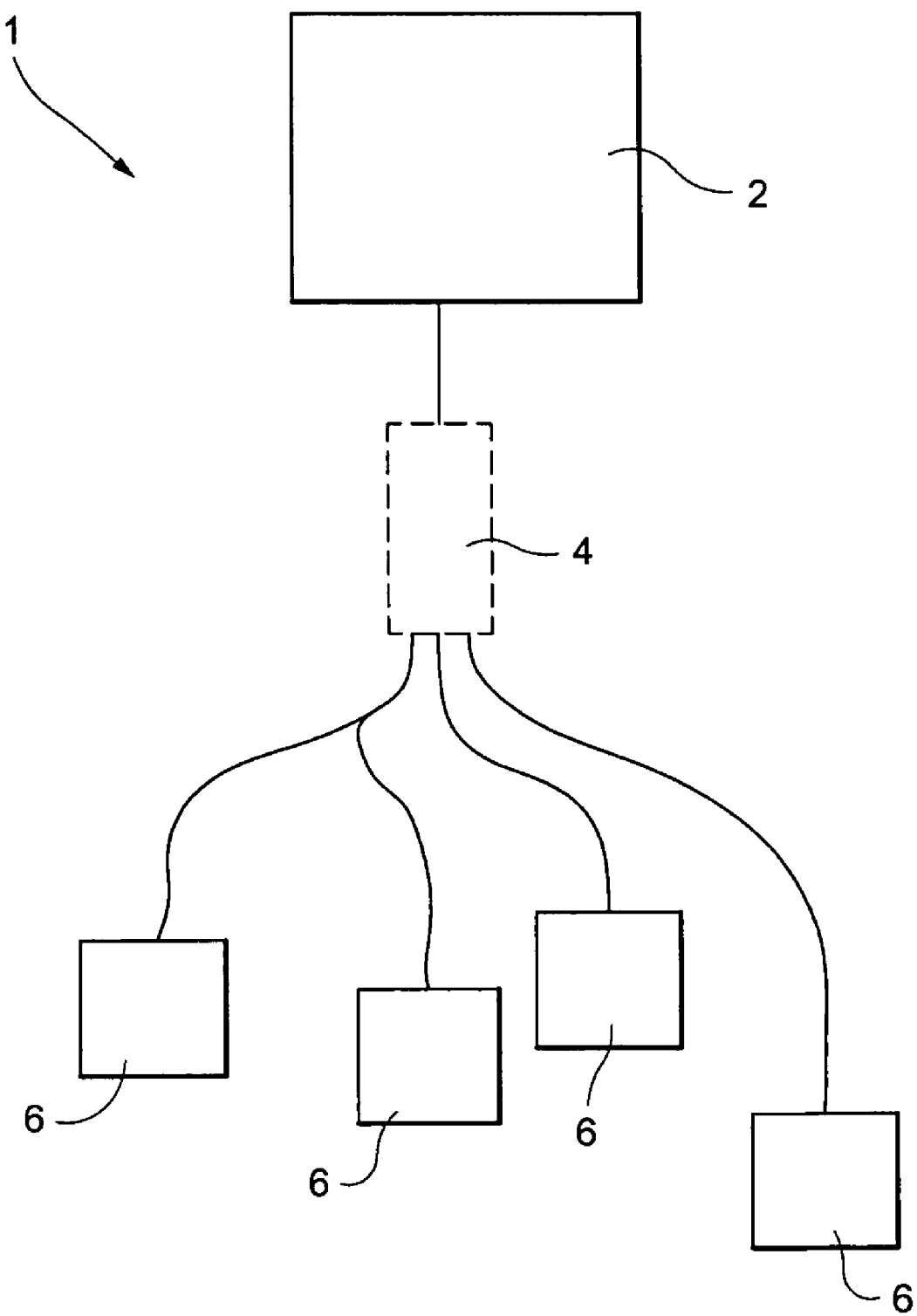
FIG. 1 is a schematic block diagram illustrating a mask fitting system according to a preferred embodiment of the invention.

A mask fitting system 1 according to an embodiment of the present invention is illustrated schematically in FIG. 1. Mask fitting system 1 includes a mask fitting database 2, one or more terminals 6, and a communication channel 4 between database 2 and terminals 6.

Mask fitting database 2 is provided to store data on a plurality of commercially available mask systems. The database 2 may be provided directly by a manufacturer of mask systems, or may be provided by a third party with the relevant information being obtained from the manufacturer.

Communication channel 4 allows communication between the database 2 and terminals 6, which may be remotely located from database 2. Communication channel 4 may be embodied in any suitable manner, for instance, wireless or land telecom line. Communication channel 4 may encompass direct hosting of the database, e.g., database, channel and a terminal may be included in a single PC system.

Channel 4 can be any known or later developed device or system for connecting each terminal 6 to the database 2, including a direct cable connection, a connection over a wide area network or a local area network, a connection over an intranet, a connection over the Internet, or a connection over any distributed processing network or system. In general, the channel 4 can be any known or later developed connection system or structure useful to connect the terminal to the database.

Figure 2:
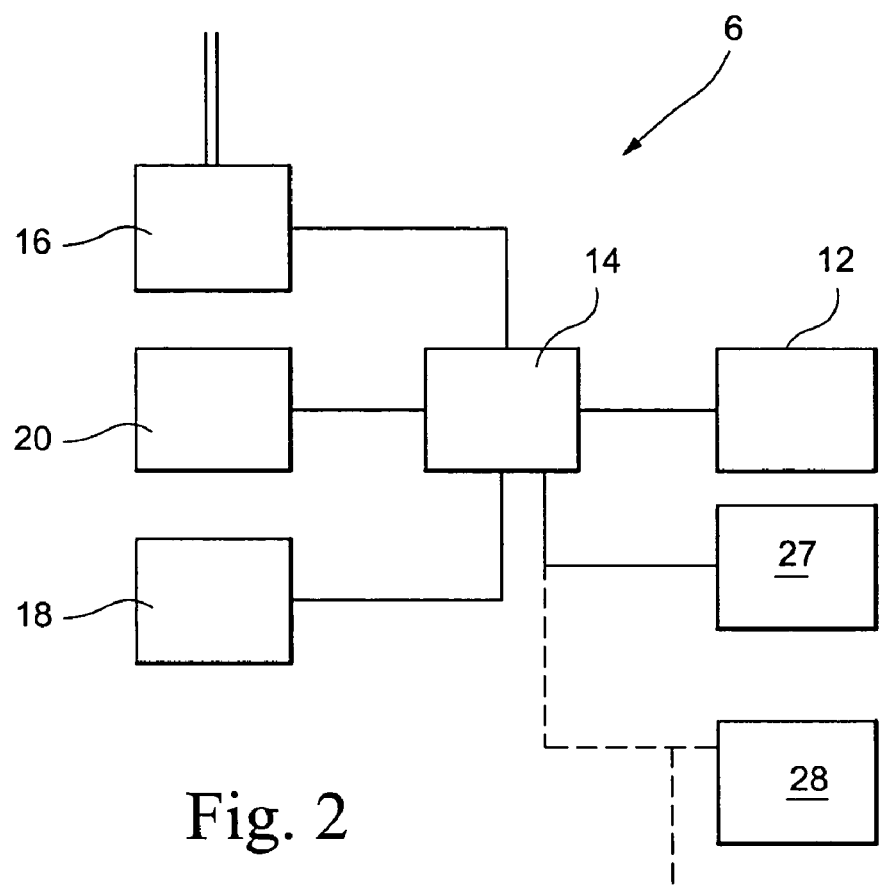
FIG. 2 is a schematic block diagram illustrating a terminal according to an embodiment of the present invention.

Terminals 6 are provided at locations where mask systems are recommended to patients, either by way of sale of the mask systems or merely dispensing them. As illustrated in FIG. 2, each terminal 6 is provided with a reader 12 by which information (patient data) from the patient may be read, received, scanned or otherwise input. A controller 14 may then communicate some or all of this data to a database 2 by means of a communication port 16.

A user interface 18, including, e.g., a monitor or display, may be provided to indicate to the user (patient, interface fitter, clinician and/or physician) the most appropriate mask system or systems for the patient. Also, terminal may have access to more general information about each mask system, and/or accessories that could be used with the recommended mask system(s). Such information can be displayed on the interface 18. Further, a memory 20 may be provided to store data relating to the patient and/or database 2, or to merely assist in the processing of the controller 14.

In one example, reader 12 could include a camera (e.g., a digital or film camera, webcam, scanner, etc.) that is provided to take images of the patient from various angles, for example, profile and/or frontal views, for measurement of various dimensions of the patient's head. This is described in more detail below in relation to FIGS. 4-8. In addition or in the alternative, the terminal may include a facial scanner 27, which is commercially available from Cyberware. Scanner 27 may use 3-D modeling techniques to scan the entire face, head, or other expected interfacing regions, or only selected portions thereof.

Other readers may include a handheld three-dimensional laser scanning device 28 which is also commercially available, e.g., the Polhemus Cobra FastScan system. This system comprises a laser, reference transmitter, data acquisition unit and software. The data from the laser and the reference transmitter is fed to a Data Acquisition Unit (DAQ). The DAQ plots the data into a 3D plane. This information can be translated using the provided software to different 3D file formats such as wrl, stl and iges.

The Polhemus Cobra FastScan scanner has an accuracy 0.5 mm and should be held at least 10 cm away from the object. The Cobra FastScan can be operated in two different modes. In the first mode it collects data as a laser sweep and 3D models are created using the data, the file format can be output in many different engineering formats the majority being either 3D mesh or point cloud. In the second mode data is collected as 3D points in an x, y and z co-ordinate system. These points are recorded to a Common Separated File (CSV) file which is a simple file that can be fed into excel or by any programmable text reader.

When scanning a person, care must be taken to ensure that the eyes are closed. Scans of people with dark skin can be difficult, in which case the laser sensitivity has to be adjusted or a white powder can be applied to the face. During scanning, the scanned person must not change his or her facial expressions, however he or she can move their head around as the reference transmitter monitors position change (it is directly connected to the DAQ).

Several non-limiting examples of output options include:
3D scan of the face via image file (wrl, stl, iges) or a test file giving reference points (csv)
Points taken at discrete positions (text file, csv).

Alternatively a stylus can be attached that is directly attached to the DAQ and can be run along the face to measure distances (e.g., nose bridge).

One or more of the following advantages of this system exist:
the profile can be stored for further use;
quick and efficient (5 minutes per scan and 10 minutes to process the scan, note: processing can be left until night)
improved accuracy with respect to hand measurement
image can be saved straight to an stl format, from which an SLA (solid) can be developed straight away
use of a design package such as ProE means that objects (e.g., masks) can be added around the scanned facial profile
measurements can be taken whilst patients are lying down.

An alternative to the Polhemus FastScan is a 3D laser scanner, which can be tripod mounted to scan 3D objects. Such laser scanners can capture the color of the object scanned with the 3D data. High accuracy lenses can be used, preferred embodiments may have an accuracy of between 50 microns to 0.5 mm. In the situation where a completed 3D head of a patient is required, the laser scanner may scan the object from a number of different angles and the scans are then stitched together with a suitable scanning software package.

Of course, other scanners, readers or input devices are also contemplated, and the embodiments are not limited to the examples provided.

For example, the scanner system may take the form of a 3D scanner that is movably mounted or relative to the patient. The 3D scanner can rotate about the patient to scan along a predetermined circular path, e.g., 0-360° or any amount in the range of 0-360°. Dental X-rays are sometimes taken with such a system. Moreover, the scanner would be stationary while the patient's support (e.g., a chair or platform) rotates.

In a preferred embodiment, the scanner preferably covers the entire head, including the individual features, e.g., ears, nostrils, etc. As further masks are developed and require new data points to be utilized, further scans would not be required. For example, in considering a new headgear sized to avoid behind the ears, the scans would already contain this data. Therefore, upgrades of masks would not require re-scanning. Moreover, using the system described below, patients who wear masks can be automatically informed, either directly or through their clinician, of new mask systems/components that are more appropriate and/or provide a better fit for the patient.

Figure 3:
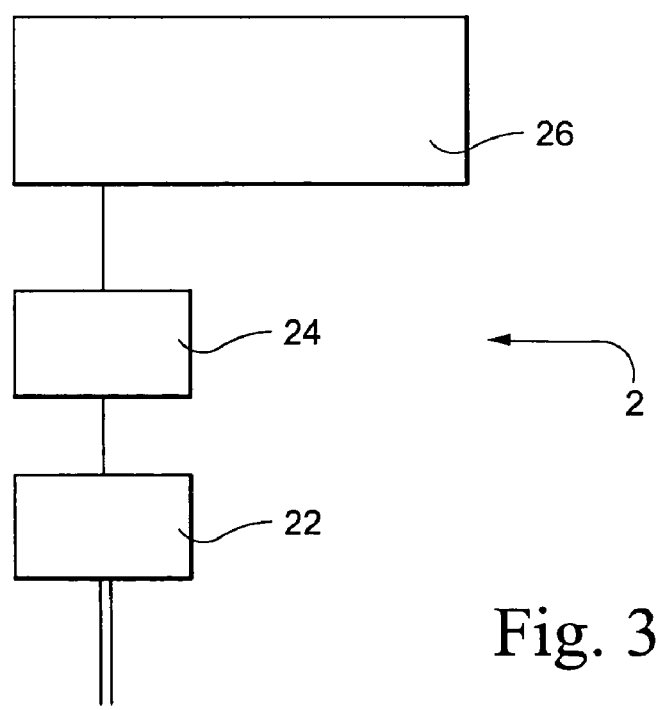
FIG. 3 is a schematic block diagram illustrating a mask system database according to an embodiment of the present invention.

FIG. 3 shows that the mask system database 2 includes a communication port 22 to allow communication with terminal 6 (FIG. 2), via channel 4. Communication port 22 may also allow communication with manufacturers for receiving data regarding mask systems. In addition, communication port 22 may receive information from other third parties, such as governmental agencies which may provide product reviews of the mask systems, possible accessories, product recalls, etc.

Mask system database 2 includes a controller 24 that interfaces with a memory 26. Memory 26 includes information (mask system data) regarding a plurality of mask systems that are commercially available. Such information includes, for example, and without limitation, data regarding the dimensions and/or weight of the mask system. Such data may also include the intended sex, age, age range, or size of patients with whom the mask system is intended for use.

In a preferred embodiment, the mask system data is based on mask system grading criteria such that mask systems with particular disadvantages or advantages are scored, rated or graded accordingly. For example, if a particular mask system is not conducive for a patient who likes to read using reading glasses when the mask system is being used, e.g., because the mask system includes an upwardly extending forehead support that may obstruct the patient's field of view and/or interfere with reading glasses, then that particular mask system would receive a lower weighted score for that particular mask system grading criteria, e.g., this mask system would receive a grade of "3" (on a scale of 1-10, 10 being the best possible grade). On the other hand, if a mask system is particularly useful for patients who have a beard and/or mustache, then the weighted score for that particular criteria will be relatively higher, e.g., a "9," when compared to other mask systems which are not particularly conducive for patients who have facial hair.

Other possible criteria includes mask size maximum fit dimensions, mouth width, nasal bridge width or depth, total nose depth, nose length, nostril spanning/sparring and angle, ear position, circumference or width of head, etc. Additional mask system grading criteria is described below.

In general, several medically acceptable mask system criteria can be established for universally grading any given mask system in a consistent manner. Such criteria can be used to establish database 2, shown in FIG. 2. In one embodiment, each mask/accessory can be provided with a tagging device, e.g., a bar code, uniform product code, RFID, etc., with data relating to product description, code, batch, purchase, etc. The information from the tagging device may be read and input into the database.

In addition to or in the alternative of using grading by best dimensions, etc., grading by "elimination" may also be used. For example, the questionnaire (an example of which is described below in FIG. 5) reduces the number of mask options to select from by eliminating non-appropriate masks. Therefore, improved accuracy and speed of selection can be achieved by selecting from a smaller pool of potential masks.

In operation, the mask fitting system 1 is configured to produce a best-fit mask fitting result which is indicative of one or more commercially available mask systems that would be most appropriate for the patient. The result is generated in accordance with a comparison of patient data (received at terminal 6) with mask system data (stored in mask system database 2). The comparison may be performed by the controller of the terminal 6, the controller of database 2, or a combination thereof.

FIGS. 4, 5, 6, 7A, 7B and 8 illustrate sequential screen shots of a mask fitting system according to an embodiment of the present invention. In general, the process includes the entry of patient details, filling out of a questionnaire, imaging, dimensioning and then recommending a mask.

Figures 4, 5:
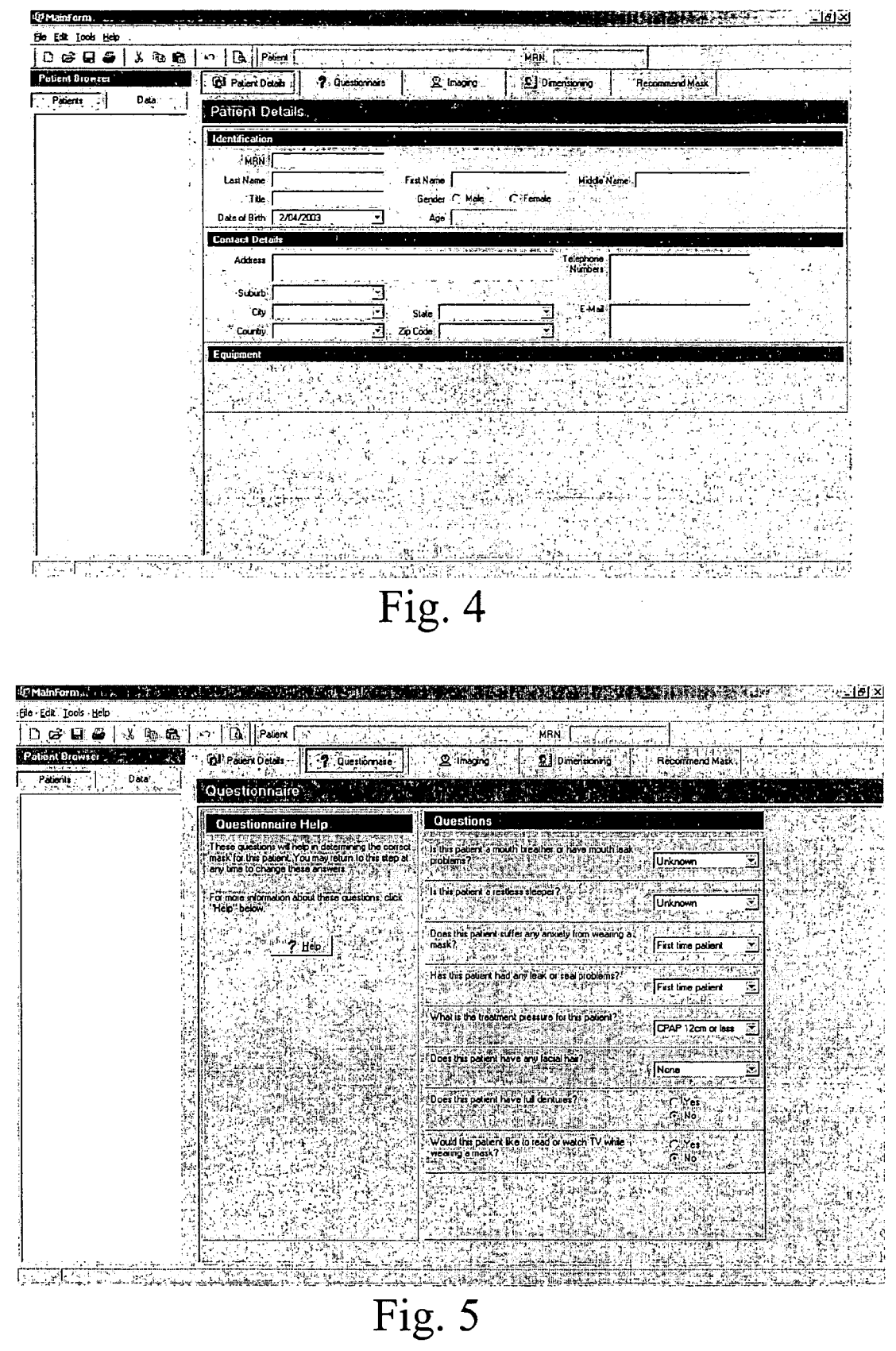

FIG. 4 is a screen shot displaying entry blocks for patient details, such as name, age, data of birth, etc.

FIG. 5 is a questionnaire which includes several questions which are answered by the patient or clinician. Generally speaking, the questionnaire is used to accumulate patient data unique to the patient. Patient data may include, but is not limited to, physical characteristics, prior history of mask use, the patient's sleeping characteristics and/or the patient's relevant facial and/or head dimensions. Physical characteristics may include the patient's age, whether the patient wears glasses, whether the patient has facial hair, whether the patient wears dentures, and/or whether the patient is male or female.

The prior history of mask use may include the type of breathing the patient normally experiences, e.g., mouth breathing or nose breathing. Other criteria may include whether the patient has in the past experienced leak problems or anxiety when wearing the mask. Additional criteria may include information as to whether the patient likes to watch TV or read while wearing the mask, prior to sleep.

Sleep characteristics may include information about the typical sleep patterns of the patient, e.g., whether the patient is a restless sleeper, which may affect stability of the mask; stability may be yet another criteria built into the database.

A sample questionnaire is provided below and may include the following questions:

Mask Grading Criteria
1. Whether the patient is a new patient.
   a. Yes
   b. No
2. Degree of mouth—nose breathing
   a. Unknown/First time patient
   b. Nose breather
   c. Mostly nose
   d. Moderate mouth
   e. Mostly mouth
   f. Mouth breather
3. Degree of restless during sleep
   a. Not restless
   b. Light restlessness
   c. Some restlessness
   d. Heavy restlessness
   e. Extreme sensitivity
4. Degree of anxiety from wearing a mask
   a. Unknown/First time patient
   b. None
   c. Slight distraction
   d. Moderate distraction
   e. High discomfort
   f. Claustrophobia
5. Does the patient have a moustache?
   a. Yes
   b. No
6. Does the patient have a beard?
   a. Yes
   b. No
7. Does the patient have any mask leak or seal problems?
   a. Unknown/First time patient
   b. No leaks
   c. Light leakage
   d. Moderate leak
   e. Heavy leak
   f. Extreme leak
8. What treatment pressure does the patient require?
   a. CPAP 12 or less
   b. CPAP greater than 12
   c. Bilevel 9. Does the patient have full dentures?
   a. Yes
   b. No
10. Does the patient want to read or watch TV with the mask on?
    a. Yes
    b. No The mask grading system/algorithm is adaptable, so that new grading criteria or changes to the existing criteria can be implemented simply by updating the database, without the need to change the rest of the system. The user questions may form a part of the overall fitting system algorithm, as shown, e.g., in FIG. 16.

Mask Grading System Example

In the example below, the following answers to the grading selection criteria, produce the mask system grading shown below for currently available mask systems. In this example, all of the mask examples are ResMed's although other masks could be included.

| 1 First time patient? | No |
| 2 Mouth leak or mouth breather? | All nose |
| 3 Restless sleeper? (Instability due to movement) | Extreme sensitivity |
| 4 Anxiety from wearing masks? | Claustrophobia |
| 5 Facial Hair - Moustache? | Yes |
| 6 Facial Hair - Beard? (Full Beard) | Yes |
| 7 Leaks or seal problems? (For refits) | Extreme Leak |
| 8 Treatment pressure? | CPAP 12 or less |
| 9 Full dentures? | No |
| 10 Read/Watch TV with mask on? | No |

| Mask System | FFM | Vista | Activa | Ultra | Swift |
|---|---|---|---|---|---|
| Score | 30 | 125 | 175 | 130 | 165 |

Mask Grading System —Mask Dimensions

To determine the best possible fit among the available mask sizes currently stored in the database, the measured patient dimensions are compared with the relevant dimensions and/or characteristics of the stored mask sizes.

A preferred embodiment of the invention grades mask sizes by comparing the measured patient facial dimensions with the nominal "best fit" dimensions stored for each mask size in the database. However, other methods, such as those using statistical techniques can also be used.

For example, relevant dimensions of the mask system can be scanned, much in the way of a patient's dimensions may be scanned. In particular, the face contacting portion of a plurality of mask interfaces may be scanned, so as to capture the various topographical features of the mask, e.g., depth, width, contour, etc. This information can be stored in a database or registry. Further, the patient's facial features (which can be scanned as well) can be compared against the scanned patient interfaces and a best fit scenario may be obtained using, e.g., statistical analyses methods. Moreover, the results of the comparison can simply be used as one metric or criteria of fit, which can be weighted relative to other metrics and/or criteria (e.g., the patient's questionnaire, etc.).

Figure 17:
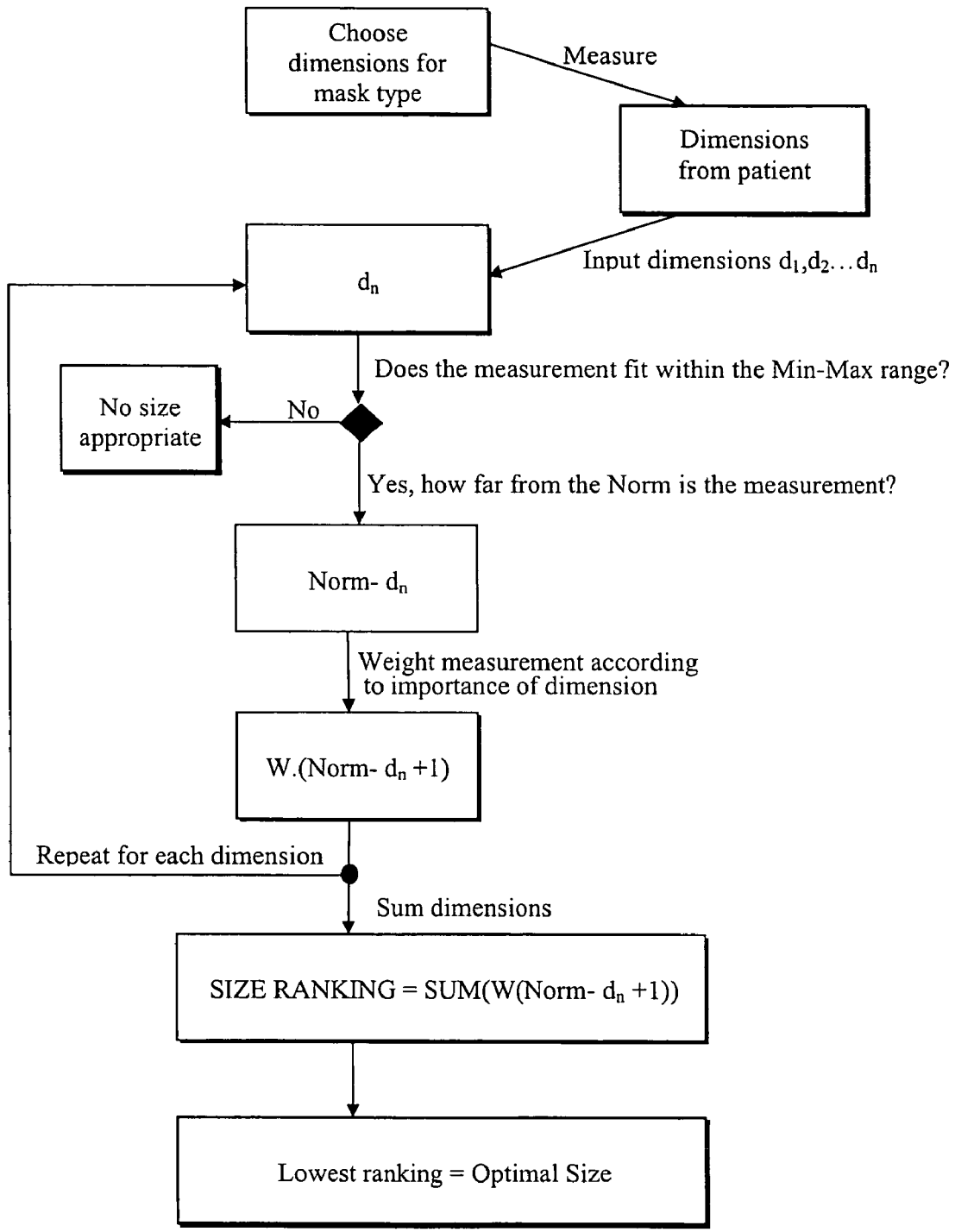
FIG. 17 is a flow chart illustrating a mask fitting algorithm according to an embodiment of the present invention.

The patient dimensions include, but ate not limited to one or more of the following:
1. Nasal bridge width
2. Nasal root depth
3. Mid-nasal bridge width
4. Mid-nasal bridge height
5. Nasal width
6. Nose tip protrusion
7. Mouth width
8. Facial height
9. Nasal height Dimensions which are necessary to fit a mask system to a patient vary, depending on the type of mask system involved. For example, a nose mask may require different information than is required for a full face mask or mask systems using cannula, nozzles, puffs, etc. FIG. 17, which is more fully described below, illustrates a sample mask fitting algorithm.

In one embodiment, the dimensions of the patient's head can be simply measured with a template or ruler and input into the terminal 6. However, FIGS. 6, 7A and 7B show a more preferred embodiment, in which one or more images of the patient are obtained (by capturing the image), and then dimensions of the patient's head are obtained (in response to user input).

Figure 6:
Figure 7A:
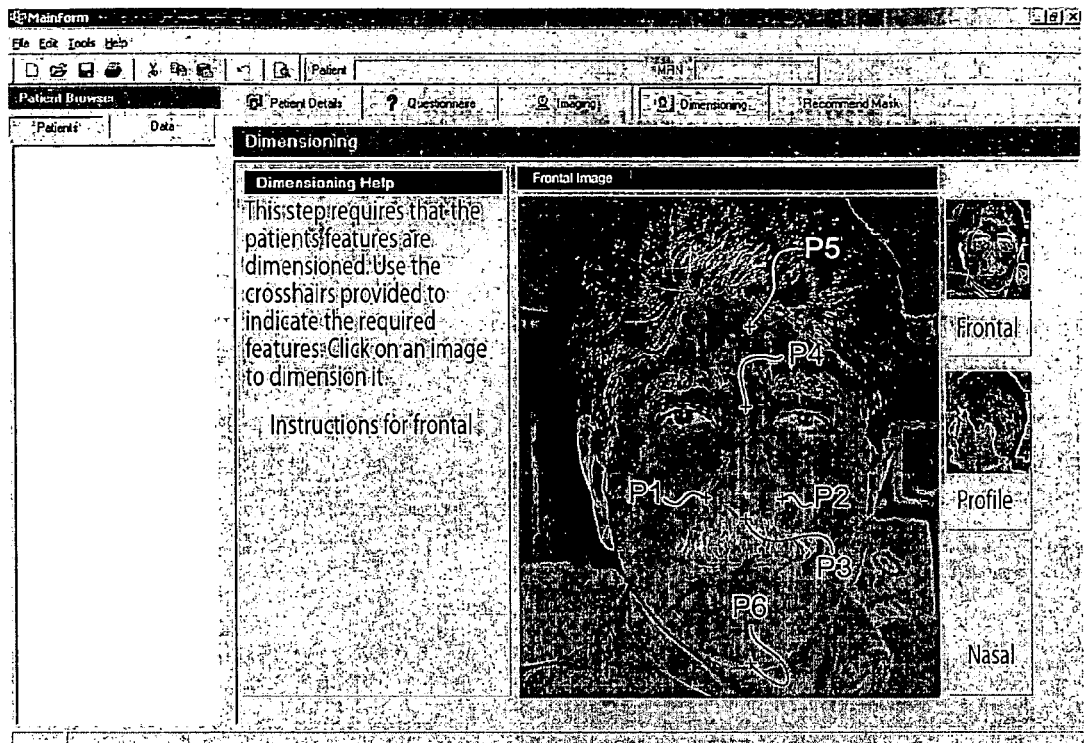
Figure 7B:
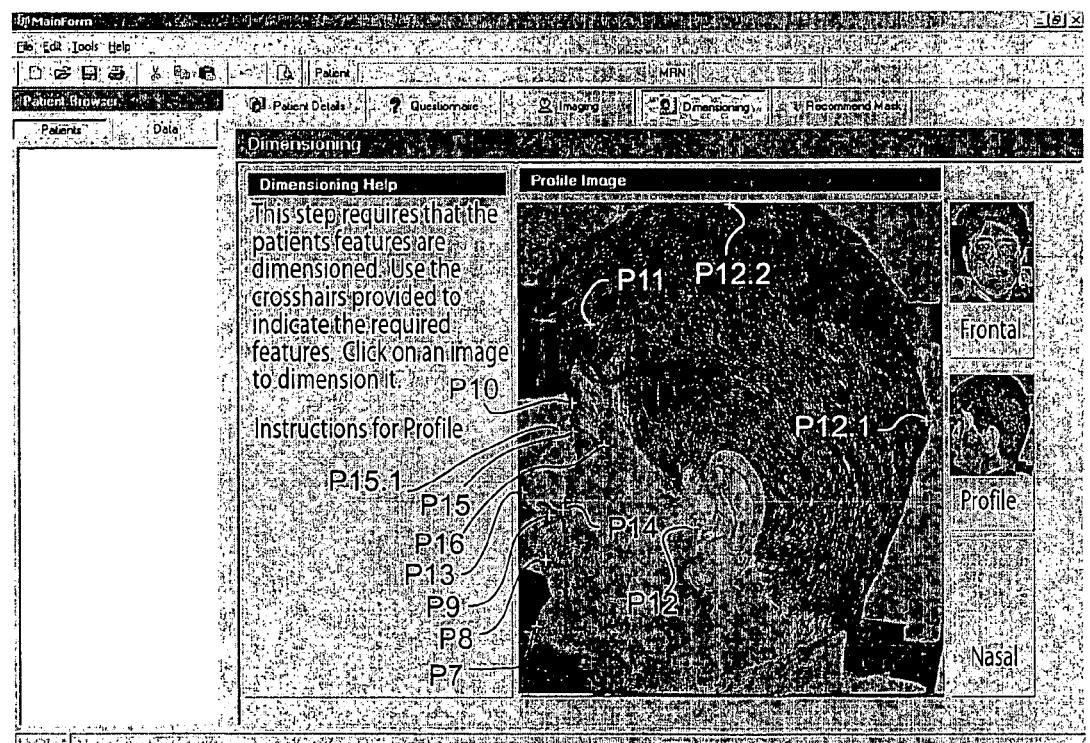
Figures 1, 7B:
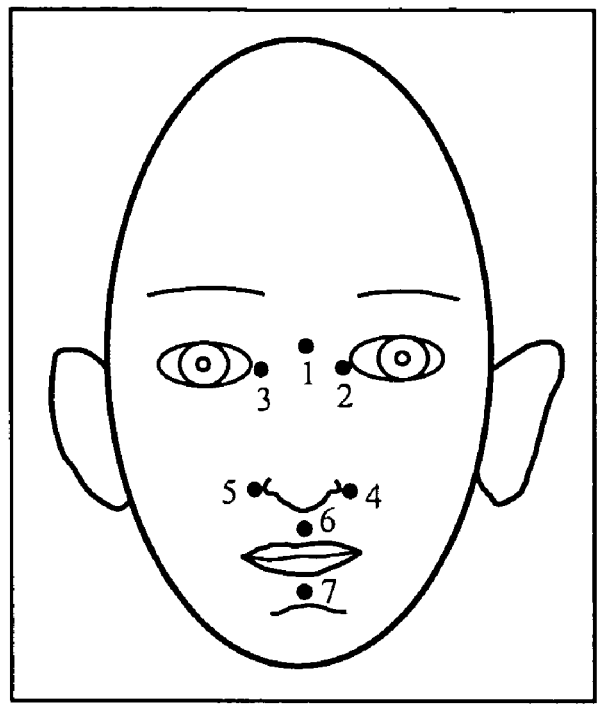
Figures 2, 7B:
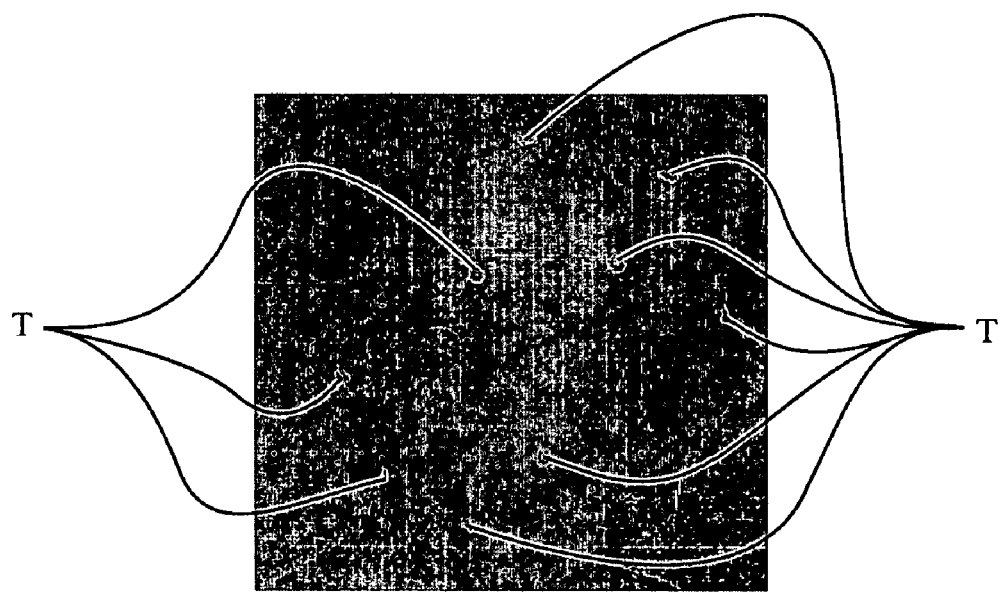
Figures 3, 7B:
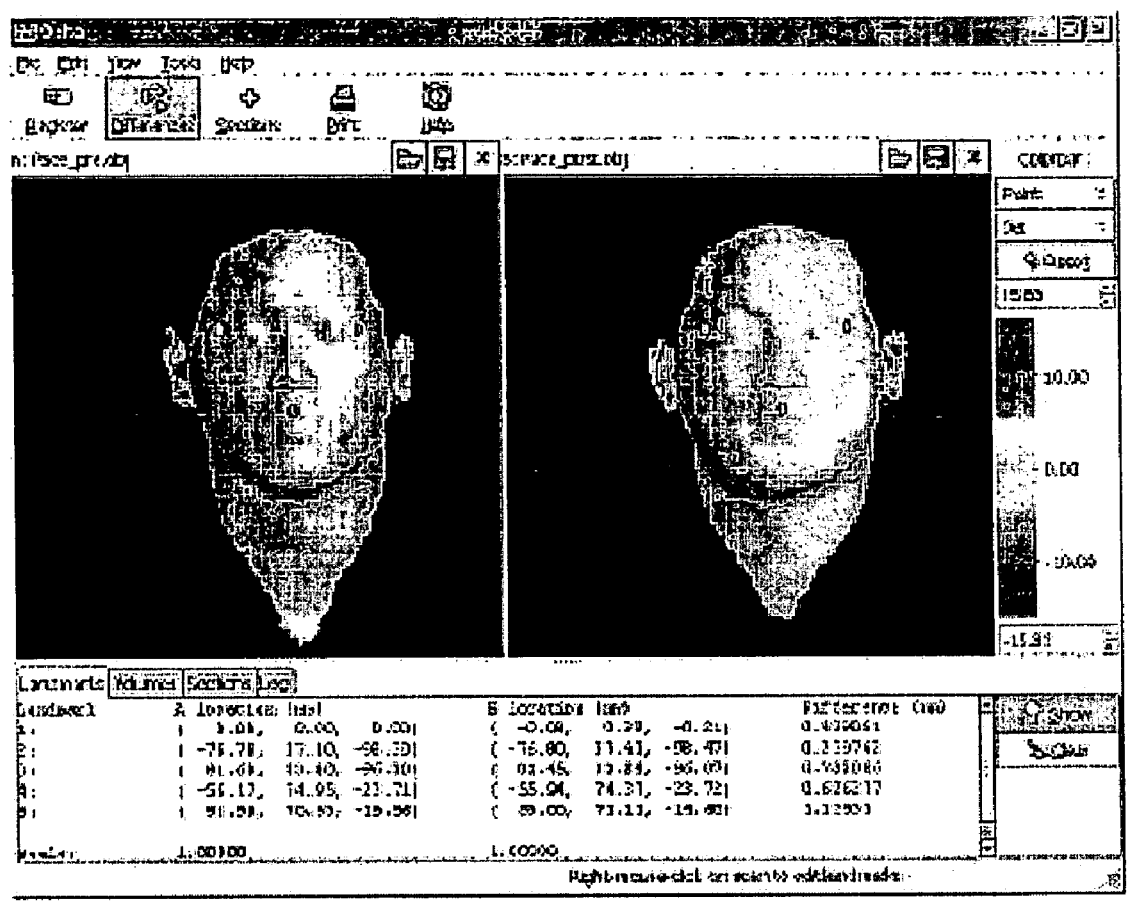

In the screenshot shown in FIG. 6, one or more images of the patient are captured and displayed on a display screen at terminal 6. The image(s) can be created using, e.g., a digital or film camera, webcam, still imaging system, and/or any system able to capture images by screen "grabbing" or video still capture, any of which may be the reader 12 described in relation to FIG. 2 above. The screenshot shown in FIG. 6 may include instructions on how to use a reader to create the recommended images.

In this embodiment, frontal and profile images of the patient are provided. However, nasal or other views can be incorporated as desired. Moreover, any reader that can transfer real time mask interfacing regions of a patient's body is readable into physical dimensions, e.g., overall dimensions or at least one plane (e.g., frontal view) can provide overall dimensions, such as nose width and head width.

After the imaging step, user input is utilized to obtain one or more dimensions from the patient's front and/or profile images. Once the image appears on the screen, as shown in FIGS. 7A and/or 7B, the patient or clinician is prompted to use the cursor to align crosshairs on the screen with various points on the patient's face. Different points will be recommended depending on whether the patient prefers nose masks or full face masks, etc. However, if the patient or clinician desires that all types of masks be considered in the selection process, then all the suggested dimensions should be entered and/or considered.

As shown in FIG. 7A, the cursor, e.g., in the shape of a crosshair, is moved to several points on the face and "clicked" so as to derive the relative dimensions for entry into the system. For example, points P1 and P2 correspond to the sidewalls of the nostrils, i.e., the widest point of the patient's nose. Selection of additional points may result in an even better mask fit, although additional data points may not be necessary, depending on the type of mask of interest. For example, the following points can be measured to provide the best possible mask fit: point P3 (the bottom tip of the nose), point P4 (on the nasal bridge between the eyes, point P5 (the middle of the patient's forehead) and point P6 (the patient's chin), etc.

It is preferable that a comprehensive set of dimensions be obtained so that if a patient needs a full face mask, as opposed to a nasal mask, the clinician/dealer could recommend a new mask without the patient returning for a subsequent fit.

The same process is repeated for the profile image of the patient, as shown on the display in FIG. 7B. Of course, the profile image point(s) could be entered first, followed by the frontal image point(s). Using the profile image, the clinician or user will then be prompted to use the cursor to "click" on a number of points on the patient's head. For example, points P7-P16 are illustrative of the points which the patient may be prompted to enter into the system. P7-P16 are generally described as follows: P7 (chin), P8 (lips), P9 (joint between upper lip and bottom of nose), P10 (bottom of forehead), P11 (top of forehead), P12 (front of ear), P12.1 (rear of head), P12.2 (top of patient's head), P13 (tip of nose), P14 (joint between cheeks and base of nose), P15 (base of nasal bridge), P15.1 (peak of bridge between eyes), P16 (rear of eye socket where temple begins). Other points and/or dimensions could be added as desired.

Some of these points, e.g., points P13, P14, P15 and P15.1 may be relevant to use for consideration of nose masks or full face masks, but may not be relevant to consideration for use with nasal cannula Points P10 and P11 may help with consideration of mask systems having forehead supports, by providing the slope of the patient's forehead. This information may also indicate the most appropriate adjustment setting for an adjustable forehead support, for best fit with the patient. Points P12, P12.1, P12.2 and/or P16 may be relevant for fitting a particular headgear to the patient's head.

In a preferred embodiment, frontal and profile images are all that are required to fit a mask. However, a nasal image could be used in a similar manner to the above if desired.

Figure 8:
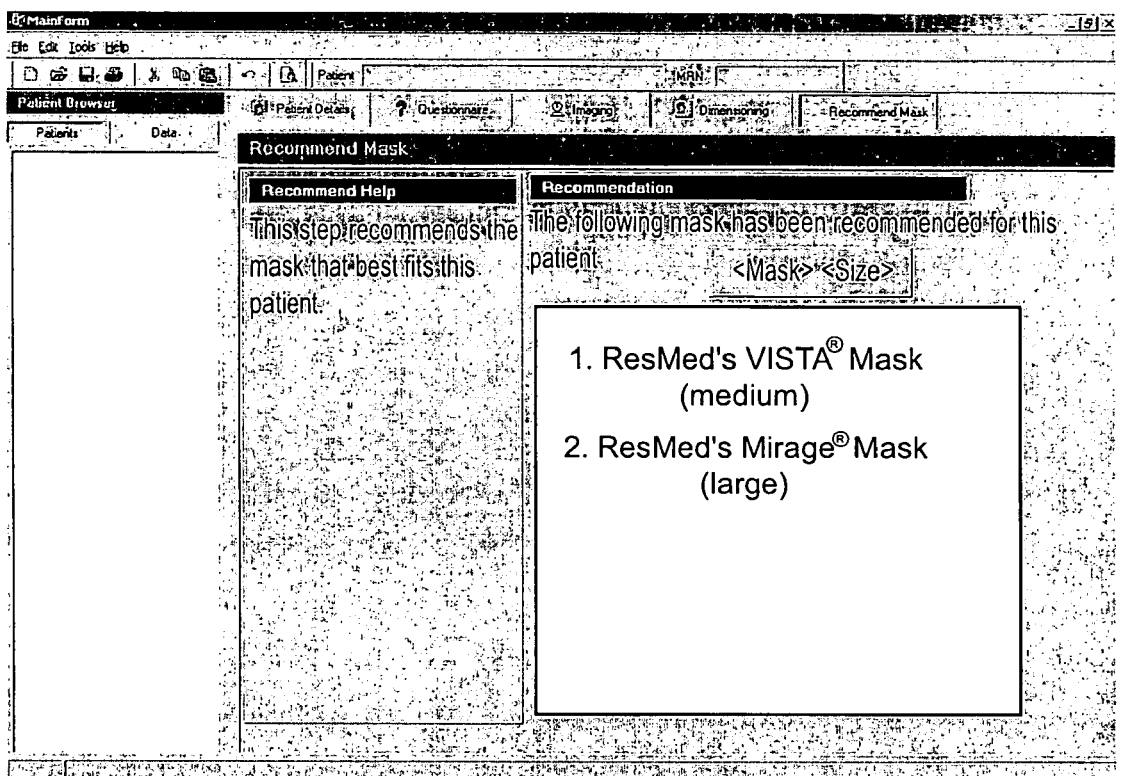

Once these suggested points are entered into the system, the fitting system may produce a best-fit mask system result See FIG. 8. The result can take the form of a single mask system which is judged to be most appropriate for the patient, or the result may include a listing of two or more masks which the patient may wish to consider. The mask fitting result may be presented in order of preference. The results page may include information about mask accessories, mask system reviews, etc., or links to such information, e.g., via database 2.

Other embodiments of the invention are shown in FIGS. 7B-1 to 7B-3. To determine the appropriate mask fit for a patient a set of predetermined points can be used that are unique to particular features of the face. FIG. 7B-1 is an example of frontal facial points that could be used to determine the appropriate mask size for a patient.

Method 1: Datum Points (e.g., Using the Polhemus Cobra FastScan)

The stylus/laser pointer would be placed on points 1-7, as shown in FIG. 7B-1, in order. Thus, data would be then sent to the software fitting program to calculate the distances between points and then a recommendation for the most appropriate mask size can be made based on the dimensions.

Method 2: Datum Points (e.g., Using the Minolta Laser Scanner)

This method uses the same concept as that outlined in Method 1 of using datum points, however instead of using a laser pointer/stylus to directly identify each point, a coloured tab T, as shown in FIG. 7B-2, is placed on selected feature points. The face is then scanned using a tripod mounted Minolta laser scanner which will map the coloured points onto a 3D model, using these points the dimensions of the patient can be found using any CAD system or CAD integrated system that is capable of importing 3D meshes. An example of software systems that could do this is Geomagic, Pro Engineer, Solid Works and IDEAS.

Method 3: Delta View (Polhemus Measuring Software)

The Delta View program (Screenshot in FIG. 7B-3), from Polhemus can be used to show how the patient's face has changed between full facial scans when the initial mask recommendation was made. Changes in the patient's weight can affect the way the mask fits onto the face the patient over time, especially in barriatric applications. This software can show geometrically how the patients face has changed and the specific areas where the most change has occurred. With this information a recommendation could be made from the software as to whether the patient requires a new mask size.

Method 4: Full Facial Scan (e.g., Using the Polhemus or Minolta Scanning Systems)

The face of the patient is scanned using the 3D laser scanner, the image is imported into a CAD package and the measurement analysis with the CAD package is used to measure the dimensions that are critical for fitting the mask.

The system may allow a clinician to override the choice, and may include "fuzzy logic" that could learn to adapt to a particular clinician's fit methods or needs. "Fuzzy logic" is optional and if included, it need not be enabled for each system user.

As described above, e.g., especially in relation to FIGS. 6-7B, the effort in taking several measurements manually is replaced with using a digital image to indicate the measurements. Preferably, the clinician or patient should align his head with a camera so as to provide for consistent and accurate results. This may be achieved by providing a template, e.g., a head support, for use with the camera. The template preferably would be fixed in relation to the camera such that the patient's head assumes a predetermined orientation. In addition, the patient's head will be preferably spaced from the camera at a predetermined distance/location, so that measurement results are consistent from patient to patient. Alternatively, the measured facial dimensions can be calibrated for each image.

Figure 8A:
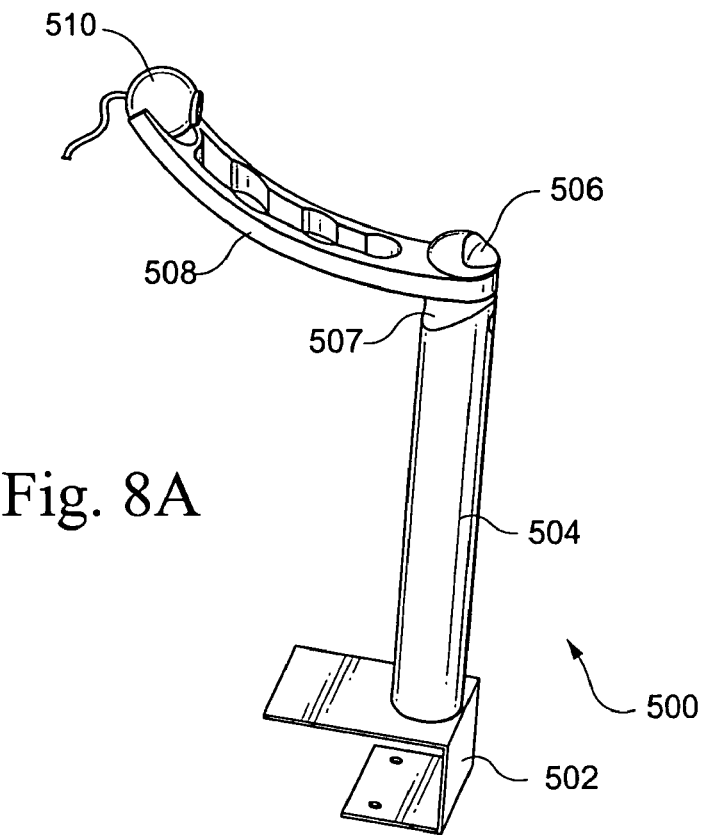
FIGS. 8A-8C illustrate a head support and camera mount according to an embodiment of the present invention.

A sample head support and camera mount assembly 500 is illustrated in FIG. 8A. Assembly 500 includes a base 502 configured to clamp onto the side of a table or desktop. Of course, base 502 could rest on the top of a table or desk. Base 502 supports an extrusion 504 with an upper end including a chin support 506 for the patient. Extrusion 504 may also support an arm 508 that is preferably pivotably mounted to the extrusion 504 via a pivot joint 507. Arm 508 includes a distal end to support an imaging device 510, e.g., a camera.

Figure 8B:
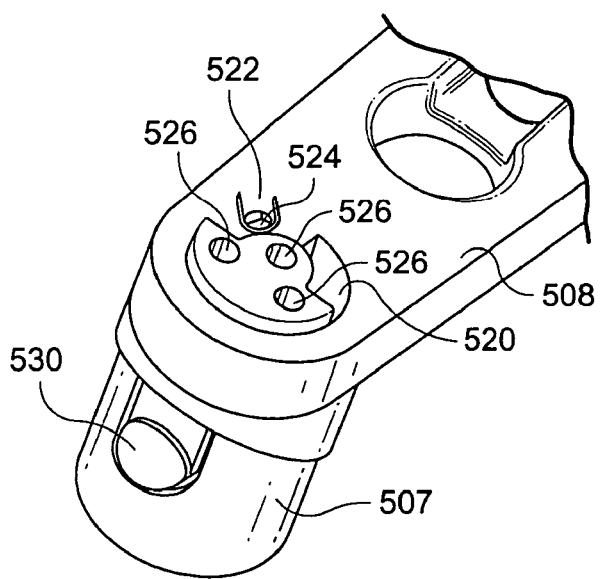
Figure 8C:
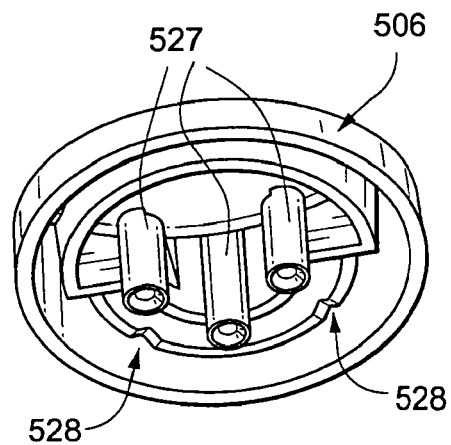

The camera mount is designed to enable consistent frontal and profile images to be taken of a patient's face when his or her head is resting on chin support 506. Imaging device 510 is supported at the end of the arm 508 attached in a fixed position, e.g., by a screw from the base and plugs at the sides. The arm 508 locates on pivot 507 and rotates through a predetermined extent, e.g., about 90 degrees. Arm 508 may lock or rotate between or into two fixed positions, e.g., by detents or the like, to provide front and profile camera images without the patient moving or disassembly of any components. Arm 508 may swing within a groove provided in pivot 507. Pivot 507 may include stops at each extreme end of the desired movement angle, e.g., about 90°. As shown in FIG. 8B, for example, the arm 508 rotates on the pivot 507 via the 90° slot 520 in the arm 508. A locking mechanism uses a small tab 522 with a bump 524 that can be seen on the arm 508: The chin rest 506 is located via projections 527 that engage with the holes 526 to clamp the arm. The tab 522 on the arm 508 deflects during rotation and the bump aligns with the notches 528 visible on the underside of the chin rest in the two 90° locations. The circular button 530 that can be seen on the pivot 507 locates the pivot by a snap fit with a hole the extrusion 504. The inclined surface between the pivot block and extrusion is one method for helping to locate the components in a uniform manner.

Chin support 506 is designed to enable a patient to comfortably rest his head and locate his face at a known fixed distance from the camera 510. Chin support 506 attaches to the pivot 507 and remains fixed when the camera arm is rotated. It is easily removable for cleaning. The arm length is designed so that the distance between the camera and patient's face is sufficient to capture all of the required facial dimensions.

Extrusion 504 is a strong and stable support column for the system. The extrusion's height above the standard desk/table enables a comfortable sitting posture for when the patient is resting his chin. The pivot 507 clips into the top of the extrusion and the other end of the extrusion is attached to a base plate/clamp 502.

Base/clamp 502 provides a secure attachment of the entire camera rig to the top of a desk or table. Camera mount can be disassembled for flat packing. Camera mount can be easily assembled by the user.

With the above system, the selection of a mask system can be very rapid. Moreover, With a wider range of mask systems, a better fit can be obtained for each patient, even those with unusual facial shapes.

The system is also advantageous in that new mask systems can be entered into the mask system database 2. This is advantageous as each patient or clinician is not required to learn or even know about each new mask, and which patients to which the new mask system is particularly suited.

This will allow clinicians to concentrate on person-to-person interactions and medical treatment, rather than struggling with measurement of the patient's dimensions, etc. The ability of the physician or clinician to introduce and recommend new products would entail better care of the patients. Moreover, patients who are fitted with the best possible mask system are more likely to use such mask system, which increases patient compliance and effectiveness of treatment.

In some applications, scaling may be required so that the dimensions are accurately entered into the system. Scaling can be achieved, for example, by a patient holding a ruler or other calibration device in the image when the frontal and/or profile views are taken. For example, the head supporting template could be provided with a built in calibration or scaling device, easily visible by the reader, e.g., scanner, camera, etc. The system can then process the image, in part by taking into account the information provided by the scaling device, e.g., a ruler or standard length. In another form, scaling can be achieved by utilizing the known focal length and/or field of view of the camera, or by clicking on a standard length scale (e.g., a ruler).

In another embodiment, the relevant dimensions of the patient's head can be automatically processed by the system, without the need for the clinician or patient to "click" on the points described above in relation to FIGS. 6-7B. In this system, the clinician or patient need only know how to operate a reader or an imaging device such as a webcam or digital camera For example, the detection of facial features can be obtained using algorithms that typically use neural networks. "SeeStorm" offers a package that detects features in the frontal image, which package is commercially available. Also, major airport security systems employ facial recognition systems/software which may automatically analyze and output desired fit dimensions, without user needing to click dimensions, thereby eliminating steps in the imaging process.

In yet another alternative, a three-dimensional modeling technique is used to determine the mask that will best fit the patient. The system would use a three-dimensional requisition device to capture a 3-D model of the patient's face. The model of the mask system is then "placed" against the model of the patient, electronically speaking, and a best fit is determined based on the minimized gap between the mask and the patient.

In yet another alterative, the 3-D modeling technique may also take into account skin texture and firmness. Once a mask fit is found, e.g., based on the above 3-D model technique for determining mask systems with minimized gap(s) between the mask system and the patient, the software will then perform an analysis for leaks and pressure at certain points around the cushion to determine the mask size that will provide maximum comfort. Fully automated facial scanners are commercially available from Cyberware. In addition, hand-held three-dimensional laser scanning devices are also commercially available. In general, both contact and non-contact imaging systems are contemplated. An example of a contact system is a multitude of pins that are slidable on a base, and which can take the impression of a patient's features.

Custom Mask Fitting

Although the above techniques include the selection of an entire mask system, similar principals can be used to select only components thereof, such as headgear, mask cushions, etc. Moreover, such information can be used to select an off-the-shelf mask system, as well as create a custom made patient interface (e.g., cushion) to replace the standard cushion provided with the mask system. Several methods for creating customized masks are described below.

Method 1: Contact Cushion Contouring (Stylus Recording)

A patient's face deforms when it is subjected to a load. For a mask to achieve the best sealing performance the contour of the mask should match the surface that it is sealing against. To develop a customized mask for a patient the shape of the mask should match the contour of the comfortable facial deformation of the patient.

Figure 9A:
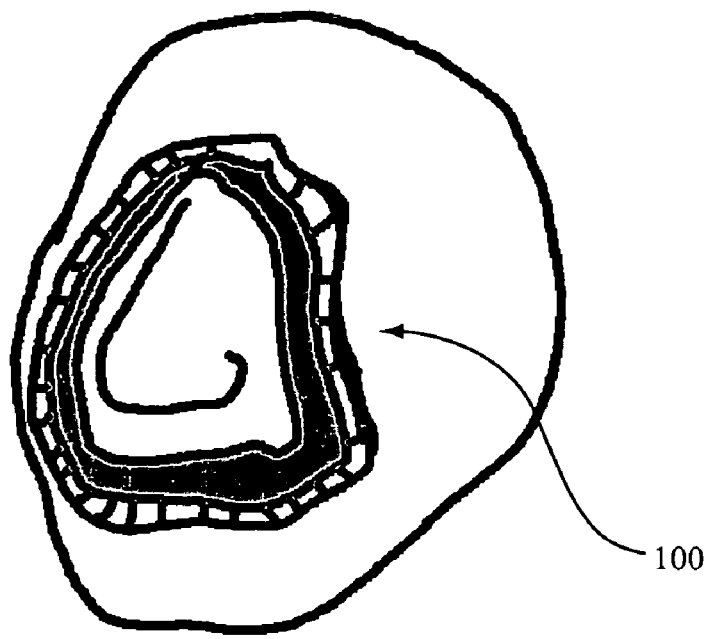
FIGS. 9A-12B schematically illustrate various custom-fit techniques according to embodiments of the present invention.
Figure 9B:
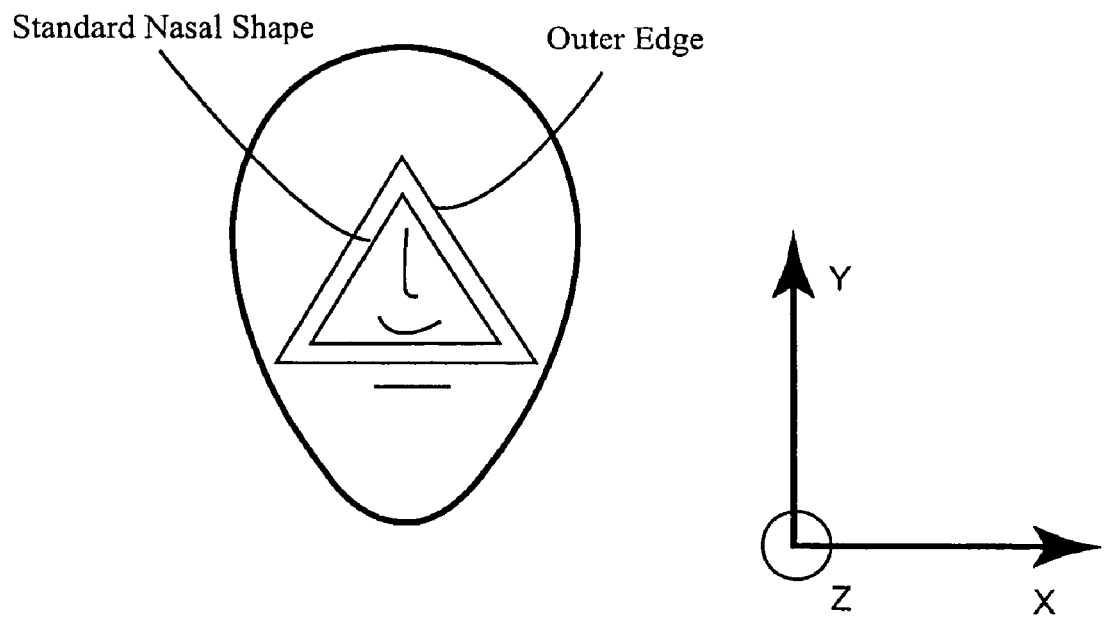

In order to find the comfortable facial deformation of the patient, a standard nasal or full face mask cushion outline can be applied. As shown in FIG. 9B, this outline is constrained in the x-y directions according to the standard cushion profiles, however, it is variable in the z direction.

Figure 10:
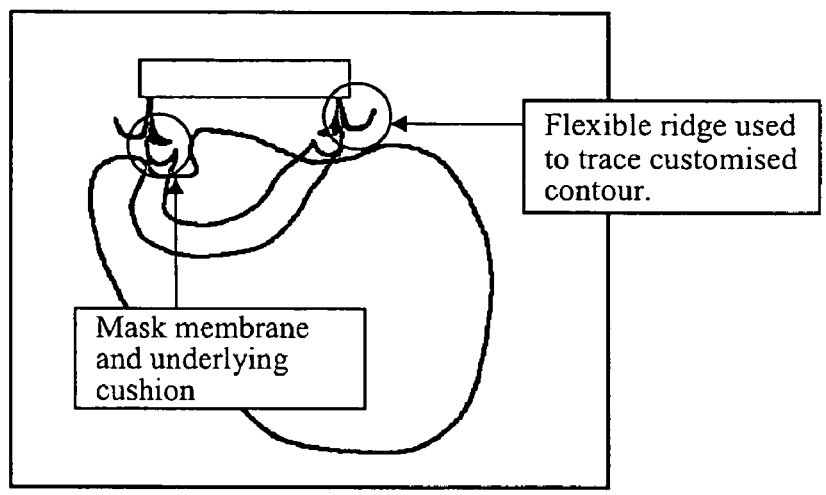
Figure 10A:
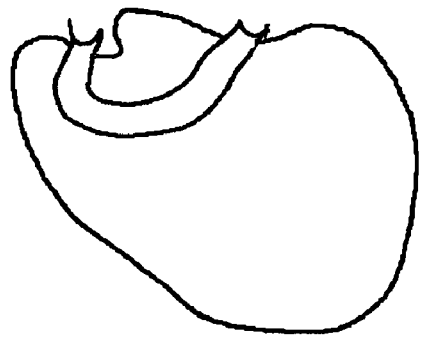
Figure 10B:
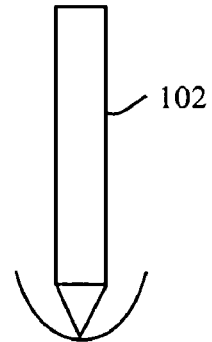
Figure 10C:
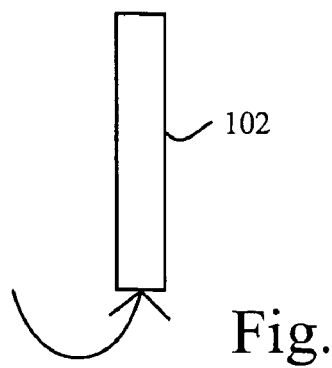

When subjected to a set pressure the outline deforms in the z direction according to the facial elasticity of each individual patient. This pressure should be equal to or exceed that required for sealing and not exceed that which is comfortable for a patient. The pressure can be produced either by a cushion or by point loads, which are controlled either by mass or a spring constant. FIGS. 9A, 10 and 10A show a mask membrane 100 and underlying cushion applied to a face. Using this outline, the stylus 102 can then be run over either the valley of the cushion (FIG. 10B) or the ridge (FIG. 10C) in order to capture the variation in the z direction data.

A further embodiment using a cushion utilizes a deformable material that changes shape when pressure is applied. The material is fitted to a standard mask frame and again has x-y dimensions matching that of standard nasal or full-face mask cushions. The frame and cushion is applied to the face at which point the deformable material varies in the z direction according to the facial elasticity of the patient. Once the frame is removed from the face, the z contour can be traced by a stylus or otherwise captured using scanning or other data capturing methods. Suitable materials include but are not limited to gel, silicone, foam or other plastic materials.

Figure 11A:
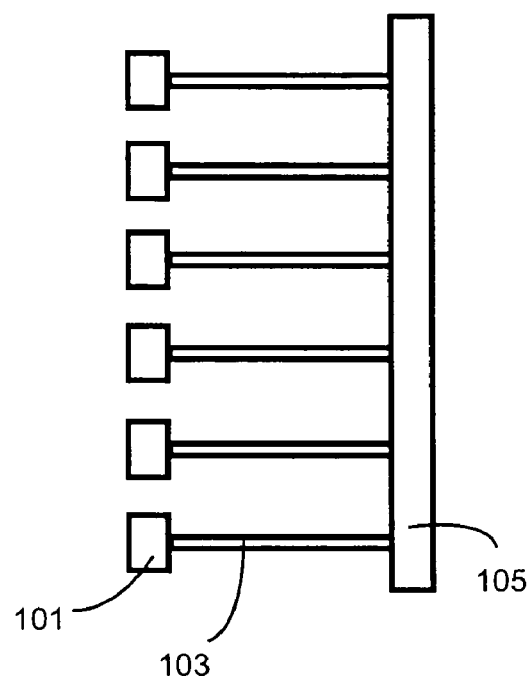

An alternative embodiment using point loads is shown in FIG. 11A. This includes a series of point loads (masses) 101 of which are mounted on rods 103 according to the preferred mask cushion outline in the directions x-y. Rods 103 are slidable on a frame 105. When fully extended as shown in FIG. 11A, the point loads have a uniform displacement in z.

Figure 11B:
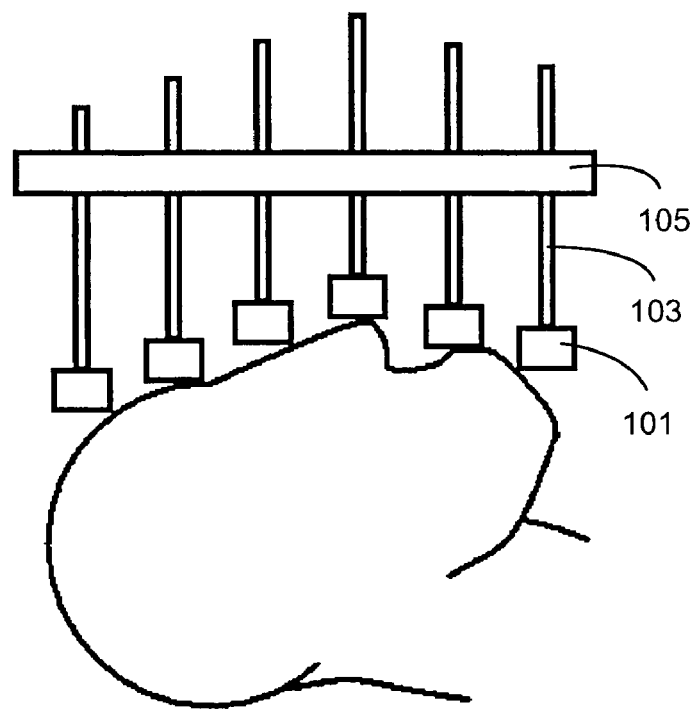

In order to apply the mass loads uniformly (due to gravity), the patient should lie on his or her back. While this may lead to some additional set-up effort, it simulates the real-life bed situation and allows for the relaxation of muscle tissue with gravity. Once the patient is comfortable, the support is moved towards the patient until all masses are resting on the patient's face, see FIG. 11B. The patient's contour can now be traced from the protruding rods using a stylus, photographic means, scanning or other data capturing methods.

Figure 11C:
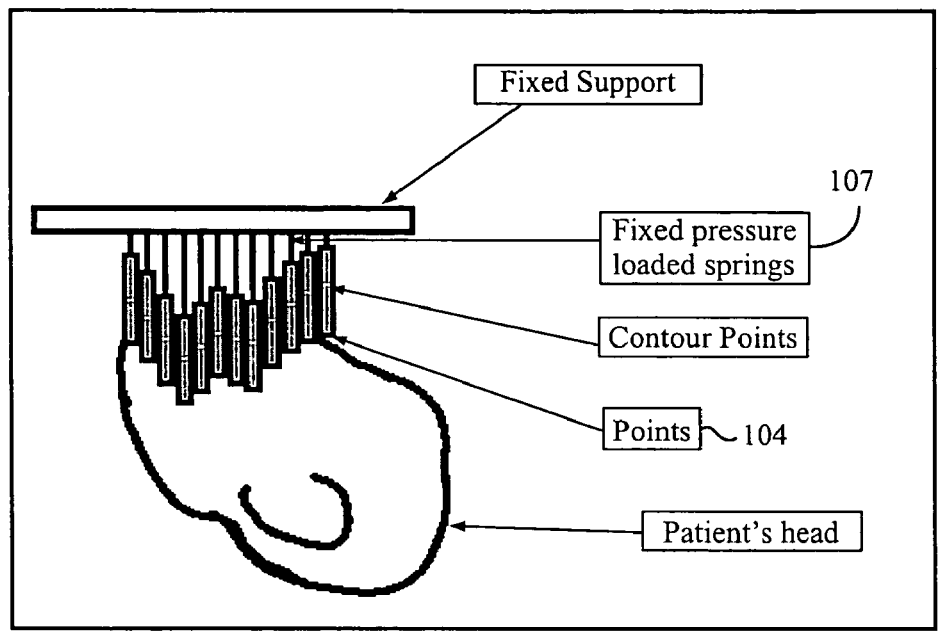

A further embodiment of the system can be set up using pre-loaded springs or a measurement of central contour points, see FIG. 11C. Such a method would not rely on the patient lying down.

An advantage of the above described systems is that they can be used on numerous patients, with only the data being sent to the mask fitting system or mask manufacturing base for conversion into a custom mask. Note, these systems as described relate only to changes in the z direction, however, similar systems can be utilized to capture data in the x and y directions providing a full knowledge of the patient geometry or completely customized cushions.

Method 2: Nasal Cannular Scan

Figure 12A:
Figure 12B:
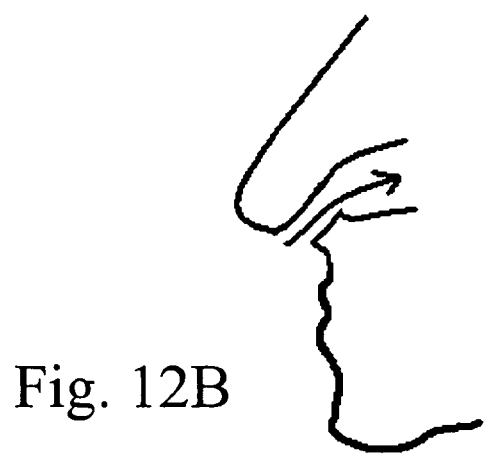

The patient's nasal area is scanned or traced with the laser/stylus and the resulting contour 106 (FIG. 12A) is used to develop customized nasal prongs. The direction of the prongs is also modified so that the airflow is placed in a direction that flows in alignment with the start of the nasal passage. FIG. 12B is a laser image of a patient's nose, e.g., the nares.

Figure 13:
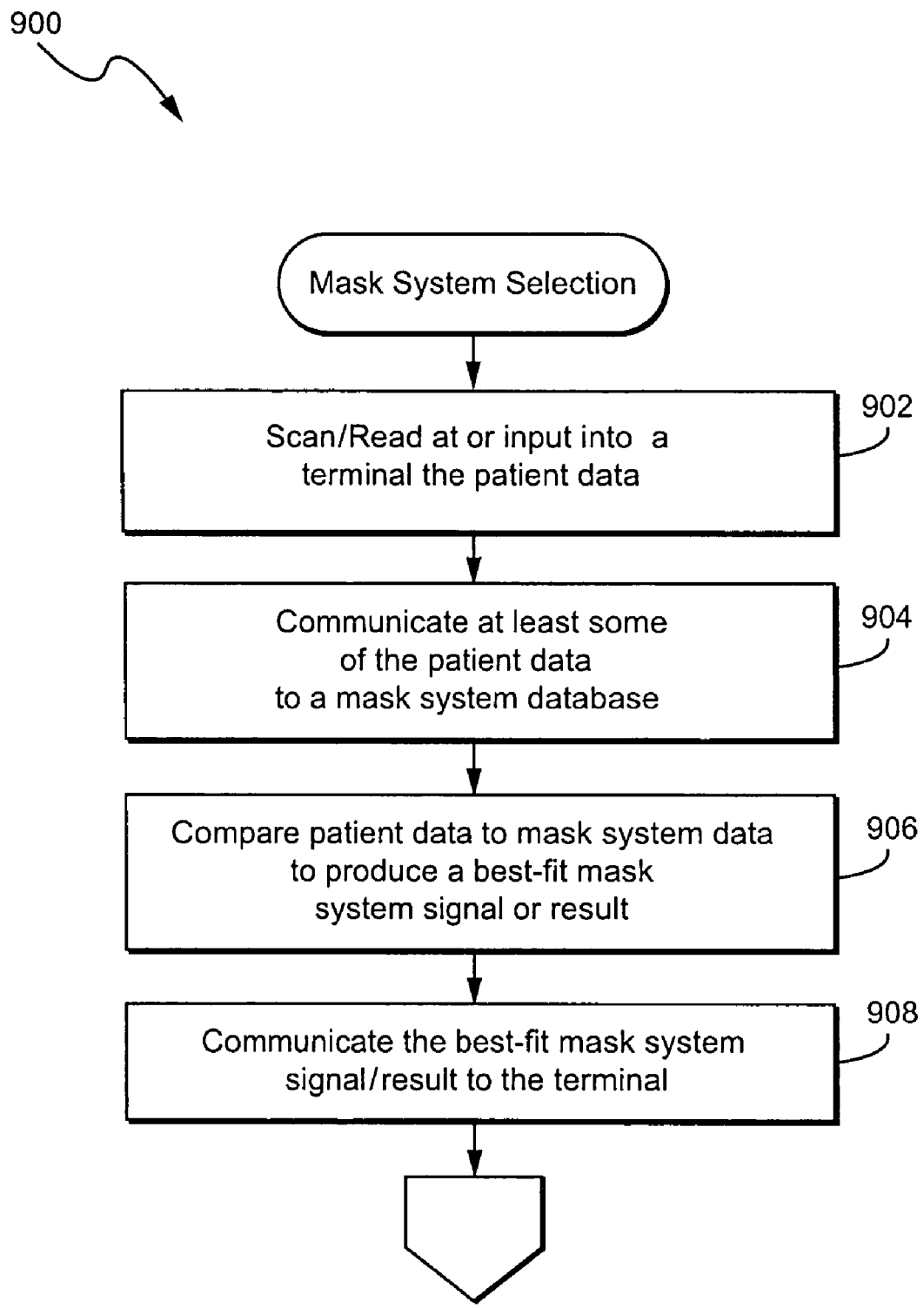
FIG. 13 is a flowchart of a mask system selection process according to an embodiment of the present invention.

FIG. 13 illustrates a process 900 for mask system selection according to an embodiment of the present invention. In step 902, patient data is scanned or read at a terminal. Alternatively, the patient data can be simply input into the terminal. In step 904, at least a portion of the patient data is communicated to a mask system database. In step 906, mask system data is compared to patient data to produce a best-fit mask system signal or result. In step 908, the best-fit mask system signal/result is communicated to the terminal.

Figures 14, 15:
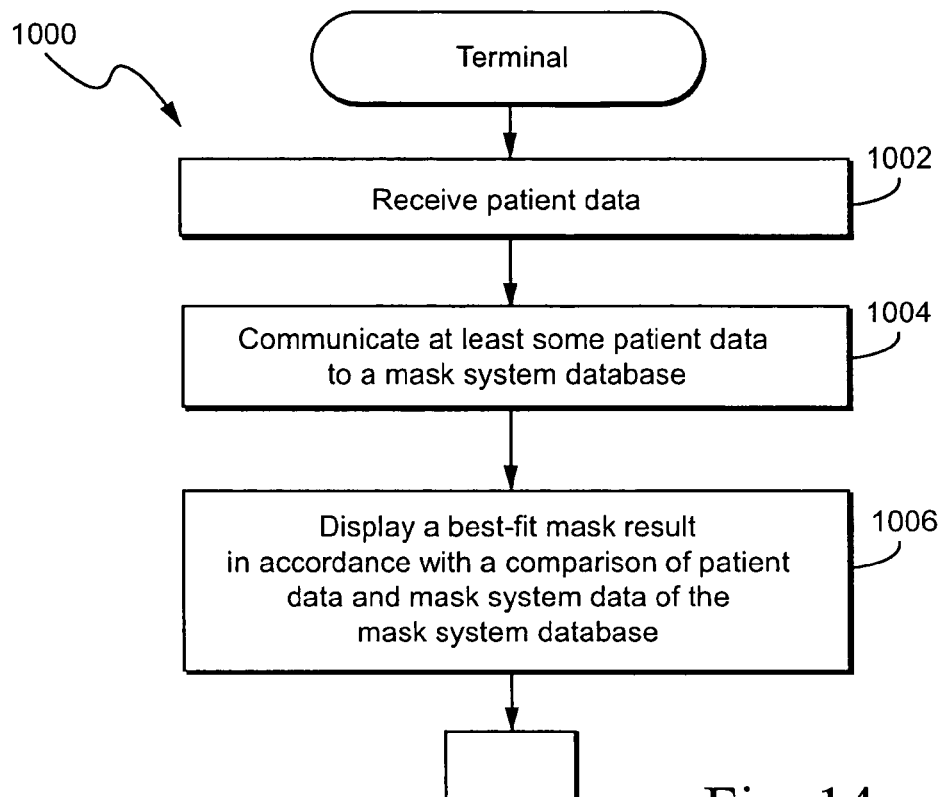
FIG. 14 is a flowchart of a terminal process according to an embodiment of the present invention.
FIG. 15 is a flowchart illustrating a mask system database process according to an embodiment of the present invention.

FIG. 14 illustrates a process 1000 for operation of terminal 6. In step 1002, patient data is received into the terminal. In step 1004, at least a portion of the patent data is communicated to a mask system database. In step 1006, a best-fit mask result is displayed at the terminal in accordance with a comparison of patient data and mask system data of the mask system database.

FIG. 15 illustrates a process 1100 for operating a mask system database. In step 1102, mask system data is stored for a plurality of mask systems. In step 1104, patient data is received from a terminal. In step 1106, a best-fit mask system result or signal is generated based on a comparison of the patient data and mask system data.

Figure 16:
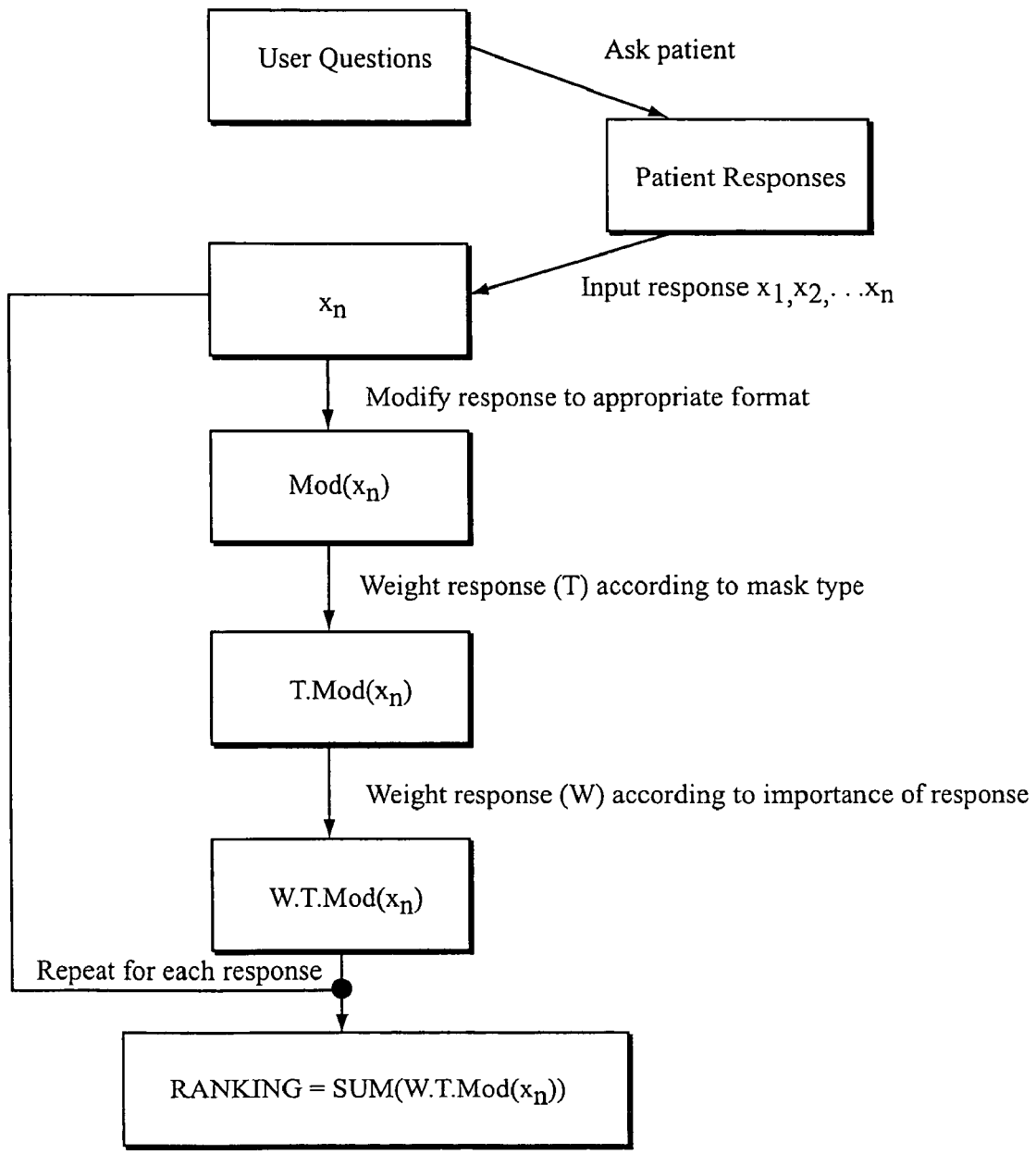
FIG. 16 is a flow chart illustrating a mask selection algorithm according to an embodiment of the present invention.

FIGS. 16 and 17 are sample flowcharts. FIG. 16 is based on mask type while FIG. 17 is based on mask size. FIGS. 16 and 17 show the process of how clinician input and designer input are captured in a sample method of weighting of the questions, and a sample method of weighting of the dimensions, respectively. The weighting of dimensions provides data for analytically describing 'goodness of fit'. Stated differently, the way in which data is produced conveniently provides the designer's expertise to the possibly inexperienced clinician fitting the mask. This may provide one or more of the following improvements to the known processes, such as fitting templates, descriptions in the user manual, etc.

Improved consistency of fit

Reduced fitting time

Reduced requirement of trial and error

Reduced reliance on clinician training

Direct incorporation of designers knowledge to the fitting method.

The flowcharts of FIGS. 13-17, or portions thereof, can be programmed onto a machine-readable recording medium, e.g., a compact or floppy disk, memory etc., that includes a control program for controlling a data processor, e.g., controllers 14 (FIG. 2) or 24 (FIG. 3). Moreover, upgrades at terminal 6 may be initiated by sending such recording medium to the terminals. Alternatively, or in addition, upgrades to the control program can be sent electronically to the terminals.

As shown in FIG. 1, the mask fitting system 1 is preferably implemented on a programmed general purpose computer. However, the mask fitting system (or its subcomponents) can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the described systems, methods and the flowcharts shown in FIGS. 13-17, can be used to implement the mask fitting system.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A mask fitting system for selecting a mask system for a patient, the system comprising:

at least one terminal configured to receive patient data specific to the patient, including at least one two-dimensional front image of the patient and at least one two-dimensional profile image, the patient data including a nasal or nares image of the patient;

an input controller in communication with the at least one terminal, the input controller being configured to determine the patient's facial dimensions from the at least one two-dimensional front image and the at least one two-dimensional profile image via an automatic facial feature extractor or pointer-based input mechanism, the automatic facial feature extractor or pointer-based input mechanism being usable to identify predefined locations on the patient's face in deriving the facial dimensions of the patient;

a mask system database to store mask system data relating to a plurality of mask systems;

a communication channel by which the patient's facial dimensions are to be communicated with the mask system database; and at least one controller configured to compare the patient's facial dimensions with the mask system data stored in the mask system database, so as to select at least one best fit mask system from the plurality of mask systems for the patient, in dependence on the comparison.

2. A mask fitting system for selecting a mask system for a patient according to claim 1, wherein the patient data includes at least one of physical characteristics, the patient's history with mask systems, and the patient's sleeping characteristics.

3. A mask fitting system for selecting a mask system for a patient according to claim 2, wherein the physical characteristics include one or more of the following criteria: age of the patient, facial hair of the patient, whether the patient wears dentures, and the sex of the patient.

4. A mask fitting system for selecting a mask system for a patient according to claim 2, wherein the patient's history with mask systems includes information regarding the patient's type of breathing, leak problems with prior mask systems, anxiety of the patient when wearing a mask system, and whether the patient prefers to watch TV or read while wearing a mask system.

5. A mask fitting system for selecting a mask system for a patient according to claim 1, wherein the facial dimensions include at least one of the depth, length and width of the patient's nose.

6. A mask fitting system for selecting a mask system for a patient according to claim 1, wherein the at least one terminal includes an automatic facial feature extractor and a user interface with a display.

7. A mask fitting system for selecting a mask system for a patient according to claim 6, wherein the terminal includes a cursor visible on the display, the cursor being configured for movement to one or more positions on the two-dimensional frontal and/or profile images of the patient, to thereby derive facial dimensions of the patient via the image(s).

8. A mask fitting system for selecting a mask system for a patient according to claim 6, wherein the automatic facial feature extractor is a scanner to automatically obtain the facial dimensions from the patient without the use of a pointer-based input mechanism.

9. A mask fitting system for selecting a mask system for a patient according to claim 1, wherein the at least one terminal is further configured to receive a separate two-dimensional nasal or nares image of the patient.

10. A mask fitting system for selecting a mask system for a patient according to claim 1, wherein the mask system data is associated with a tagging device provided on each of the mask systems.

11. A mask fitting system for selecting a mask system for a patient according to claim 1, wherein the system includes fuzzy logic to adapt to a user's fit methods.

12. A mask fitting system for selecting a mask system for a patient according to claim 1, wherein the at least one two-dimensional front image and/or the at least one two-dimensional profile image are compared to scans of the plurality of mask systems, and a metric of best fit is determined therefrom.

13. A mask fitting system for selecting a mask system for a patient according to claim 1, wherein the patient data specific to the patient includes a scan and/or a trace of the patient's nasal area.

14. A three-dimensional mask fitting system for selecting a mask system for a patient, the system comprising:
at least one terminal configured to receive patient data specific to the patient, including a three dimensional facial representation of the patient;
a mask system database to store mask system data relating to a plurality of mask systems;
a communication channel by which patient data received by the at least one terminal is to be communicated with the mask system database;
at least one controller configured to compare the three dimensional facial representation of the patient with the mask system data stored in the mask system database, the at least one controller being configured to compare the patient data with the mask system data stored in the mask system database, so as to select at least one mask system from the plurality of mask systems; and
mask fitting programmed logic circuitry configured to predict leaks and contact pressure between the at least one mask system and the three dimensional facial representation of the patient, taking into account the patient's skin texture and firmness, so as to select at least one best-fit mask system from the at least one mask system selected by the at least one controller.

15. A mask fitting system for selecting a mask system for a patient according to claim 14, wherein the terminal includes a non-contact reader to obtain the three dimensional facial representation of the patient.

16. A mask fitting system for selecting a mask system for a patient according to claim 14, wherein the terminal includes a contact reader to obtain the three dimensional facial representation of the patient.

17. A three-dimensional mask fitting system for selecting a mask system for a patient according to claim 14, further comprising a contact cushion contouring device operable to provide the three dimensional representation of the patient.

18. A three-dimensional mask fitting system for selecting a mask system for a patient according to claim 17, wherein the contact cushion contouring device is formed from a deformable material including one or more of gel, silicone, foam, and/or plastic material.

19. A three-dimensional mask fitting system for selecting a mask system for a patient according to claim 17, wherein the contact cushion contouring device comprises a cushion of pins and/or loaded springs.

20. A three-dimensional mask fitting system for selecting a mask system for a patient according to claim 17, wherein the contact cushion contouring device is configured to be placed over the patient's face to form a deformation, and further wherein the deformation may be traced, photographed, and/or scanned.

21. A mask fitting system for selecting a mask system for a patient according to claim 20, further comprising a stylus and/or laser operable to generate the scan and/or trace.

22. A mask fitting system for selecting a mask system for a patient according to claim 20, wherein the scan and/or the trace may be used to customize nasal prongs.

23. A method for selecting a mask system for a patient comprising:
receiving into a terminal patient data unique to the patient and at least one two-dimensional front image of the patient and at least one two-dimensional profile image of the patient, the patient data including a nasal or nares image of the patient;
determining patient facial dimensions from the at least one two-dimensional front image and the at least one two-dimensional profile image via an automatic facial feature extractor or pointer-based input mechanism, the automatic facial feature extractor or pointer-based input mechanism being usable to identify predefined locations on the patient's face in deriving the facial dimensions of the patient;
communicating the patient's facial dimensions to a mask system database;
comparing the patient's facial dimensions to mask system data stored in the mask system database to produce a best-fit mask system signal or result; and
communicating the best-fit mask system signal or result to the terminal.

24. A method for operating a terminal for use in determining a best fit mask system for a patient, the method comprising:

receiving patient data and at least one three dimensional facial image of the patient from the terminal;

communicating at least a portion of the patient data and a representation of the three dimensional facial image of the patient to a mask system database, the mask system database including a plurality of mask systems;

comparing the patient data and the at least one three dimensional facial image with mask system data stored in the mask system database;

selecting at least one mask system from the plurality of mask systems;

electronically determining pressure and leaks between the representation of the three dimensional facial image of the patient and each one at least one mask system of the plurality of mask systems by at least taking the texture and firmness of the patient's skin into account, so as to determine at least one best-fit mask system; and displaying the at least one best-fit mask system.

25. A method according to claim 24, further comprising receiving from a contact cushion contouring device the patient data specific to the patient, the contact cushion contouring device being formed from a deformable material including one or more of gel, silicone, foam, and/or plastic material.

26. A method according to claim 24, wherein the contact cushion contouring device comprises a cushion of pins and/or loaded springs.

27. A method according to claim 24, further comprising:
placing a contact cushion contouring device over the patient's face; and,
tracing, photographing, and/or scanning the contact cushion contouring device to generate the patient data specific to the patient.

28. A method according to claim 27, further comprising customizing nasal prongs based at least in part on the scan and/or the trace of the nasal area.

29. A method according to claim 24, further comprising scanning and/or tracing the patient's nasal area to generate patient data specific to the patient, the scanning and/or tracing being performed by a stylus and/or a laser.

30. A recording medium on which is recorded a control program for controlling a data processor used in conjunction with a mask fitting system, the recording medium including machine-readable instructions for causing the data processor to:
receive into a terminal patient data unique to a patient, including at least one two-dimensional front image of the patient and at least one two-dimensional profile image of the patient, the patient data including a nasal or nares image of the patient;
determine patient facial dimensions from the at least one two-dimensional front image and the at least one two-dimensional profile image via an automatic facial feature extractor or pointer-based input mechanism, the automatic facial feature extractor or pointer-based input mechanism being usable to identify predefined locations on the patient's face in deriving the facial dimensions of the patient;
communicate the patient's facial dimensions to a mask system database including mask system data;
compare the patient's facial dimensions with the mask system data to provide a best-fit mask system result;
communicate the best-fit mask system result from the mask system database to the terminal; and
display the at least one best-fit mask system.

31. A recording medium according to claim 30, wherein a contact cushion contouring device is operable to generate the patient data, the contact cushion contouring device being formed from a deformable material including one or more of gel, silicone, foam, and/or plastic material.

32. A recording medium on which is recorded a control program for controlling a data processor used in conjunction with a terminal of a mask fitting system, the recording medium including machine readable instructions for causing the data processor to:
read, receive, and/or scan patient data unique to a patient and at least one three dimensional facial image of the patient;
communicate at least a portion of the patient data and a representation of the three dimensional facial image of the patient to a mask system database, the mask system database including a plurality of mask systems; compare the patient data and the at least one three dimensional facial image with mask system data stored in the mask system database;
select at least one mask system from the plurality of mask systems;
electronically determine pressure and leaks between the representation of the three dimensional facial image of the patient and each one of the at least one mask system of the plurality of mask systems by at least taking the texture and firmness of the patient's skin into account, so as to determine at least one best-fit mask system; and
provide at least one best-fit mask system.

33. A recording medium on which is recorded a control program for controlling a data processor used in conjunction with the mask fitting database of a mask fitting system according to claim 32, wherein the mask system data includes individual characteristics on each of the plurality of mask systems, the individual characteristics of each of the plurality of mask systems graded according to a mask system grading criteria.

34. A recording medium according to claim 32, wherein a contact cushion contouring device is operable to generate the patient data is based on a contact cushion contouring device configured to generate input to the control program, the contact cushion contouring device comprising a cushion of pins and/or loaded springs.

35. A recording medium according to claim 32, wherein the patient data specific to the patient can be generated by tracing, photographic, and/or scanning a contact cushion contouring device placed over the patient's face.

36. A recording medium according to claim 32, wherein the patient data specific to the patient is based on a scan and/or a trace of the patient's nasal area that is provided as input to the control program.

37. A recording medium according to claim 36, wherein a stylus and/or laser is operable to generate the scan and/or trace as input to the control program.

38. A recording medium according to claim 36, wherein the scan and/or the trace may be used to customize nasal prongs.

39. A mask fitting system for selecting a mask system for a patient, the system comprising:
an image acquisition device configured to take at least two images of a patient from different pre-determined angles at a predetermined fixed focal length, the images being taken subsequent to one another; and
at least one terminal configured to receive the at least two images of a patient, the at least one terminal being configured to:
identify patient landmarks via a pointer-based input mechanism or an automatic facial feature extractor that takes into account the pre-determined angles and the predetermined fixed focal length;

compare said identified patient landmarks with dimensional data of a plurality of masks stored in a database and identify at least one mask likely or suitable to fit a patient based on said comparison, and determine and display a weighted score of likelihood of suitability of fit of each identified mask.

40. A mask fitting system according to claim 39, further comprising a mount assembly including a base for stabilizing the mount, a chin support attached to the base for locating the patient's head, an arm attached to chin support for setting the focal length, and a distal end of said arm to support said image acquisition device.

41. A mask fitting system according to claim 40, wherein the distal end of said arm comprises a screw to secure the image acquisition device.

42. A mask fitting system according to claim 40, wherein the arm is located on a pivot to rotate the arm from a first position to at least a second position.

43. A mask fitting system according to claim 42, further comprising a lock in at least a portion of the pivot to stabilize the image acquisition device in at least a first position.

44. A mask fitting system according to claim 43, wherein the lock comprises a tab and a bump.

45. A mask fitting system according to claim 43, wherein the lock stabilizes the image acquisition device at a frontal position of the patient and a profile position of the patient.

46. A mask fitting system according to claim 40, wherein the chin support remains in a fixed position when the image acquisition device is rotated.

47. A mask fitting system according to claim 40, wherein the arm is provided at a length sufficient to enable the image acquisition device to capture all required facial dimensions.

48. A mask fitting system according to claim 40, wherein the mount assembly is disassemblable.

49. A mask fitting system according to claim 39, wherein the patient landmarks include dimensions obtained from front and profile views of a patient.

50. A mask fitting system according to claim 49, wherein the dimensions include at least one of the depth, length, and width of the patient's nose.

51. A mask fitting system according to claim 50, wherein the at least one terminal comprises an automatic facial feature extractor and a user interface with a display.

52. A mask fitting system according to claim 51, wherein the automatic facial feature extractor comprises a camera configured to provide an image of the patient to the display, wherein the image comprises at least one of a frontal image of a patient, a profile image of the patient and/or a nasal or nare image of the patient.

53. A mask fitting system according to claim 39, wherein the image acquisition device is configured to provide a 3D model of the patient's face, the 3D model being usable by the at least one terminal to electronically determine possible gaps between the patient's face and the plurality of mask systems.

54. A mask fitting system according to claim 53, wherein the patient's skin texture/firmness is taken into account to determine said possible gaps.

55. A mask fitting system according to claim 39, wherein the image acquisition device includes a camera.

56. A mask fitting system according to claim 39, wherein the image acquisition device includes a 3D scanner.

57. A mask fitting system according to claim 39, wherein the at least one two images include at least one two-dimensional front image of the patient and at least one two-dimensional profile image, including a nasal or nares image of the patient.

58. A mask fitting system according to claim 39, wherein the at least one terminal is further configured to identify said patient landmarks via a scanner or cursor-based input mechanism.

59. A mask fitting system according to claim 39, wherein the at least one terminal is further configured to receive a separate two-dimensional nasal or nares image of the patient.

60. A mask fitting system according to claim 39, wherein the terminal includes a cursor visible on the display, the cursor being configured for movement to one or more positions on the two-dimensional frontal and/or profile images of the patient, to thereby derive facial dimensions of the patient via the image(s).

61. A mask fitting system according to claim 39, wherein the automatic facial feature extractor is a scanner to automatically obtain the facial dimensions from the patient without the use of a cursor.

\* \* \* \* \*